(12) United States Patent
Bliss et al.

(10) Patent No.: US 9,387,039 B2
(45) Date of Patent: Jul. 12, 2016

(54) AORTIC DISSECTION SEPTAL CUTTING TOOL

(71) Applicant: W. L. Gore & Associates, Inc., Newark, DE (US)

(72) Inventors: Cody L. Bliss, South Jordan, UT (US); Edward H. Cully, Flagstaff, AZ (US); Michael D. Dake, Stanford, CA (US); Joel M. Greene, Flagstaff, AZ (US); Joshua J. Lovekamp, Flagstaff, AZ (US); Michael C. Nilson, Flagstaff, AZ (US); Himanshu J. Patel, Ann Arbor, MI (US); David M. Williams, Ann Arbor, MI (US); William P. Witort, Berkeley, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/798,209

(22) Filed: Jul. 13, 2015

(65) Prior Publication Data
US 2015/0313626 A1  Nov. 5, 2015

Related U.S. Application Data

(63) Continuation of application No. 14/023,109, filed on Sep. 10, 2013, now Pat. No. 9,107,681, which is a continuation of application No. 12/944,623, filed on Nov. 11, 2010, now Pat. No. 8,556,921, which is a continuation-in-part of application No. 12/620,360, filed on Nov. 17, 2009, now Pat. No. 8,491,613.

(51) Int. Cl.
| | | |
|---|---|---|
| *A61B 17/32* | (2006.01) |
| *A61B 18/18* | (2006.01) |
| *A61B 17/3201* | (2006.01) |
| *A61B 18/14* | (2006.01) |
| *A61B 17/3207* | (2006.01) |
| *A61B 17/00* | (2006.01) |
| *A61B 17/22* | (2006.01) |

(52) U.S. Cl.
CPC ............. *A61B 18/18* (2013.01); *A61B 17/3201* (2013.01); *A61B 17/320016* (2013.01); *A61B 18/1492* (2013.01); *A61B 17/32075* (2013.01); *A61B 2017/00778* (2013.01); *A61B 2017/22052* (2013.01); *A61B 2017/22069* (2013.01)

(58) Field of Classification Search
CPC ................. A61B 17/32075; A61B 17/320783; A61B 17/320758; A61B 2017/320004; A61B 2017/00778; A61B 2017/22052; A61B 18/18
See application file for complete search history.

(56) References Cited

U.S. PATENT DOCUMENTS

| | | |
|---|---|---|
| 3,704,711 A | 12/1972 | Park |
| 5,053,044 A | 10/1991 | Mueller et al. |
| 5,152,771 A | 10/1992 | Sabbaghian et al. |
| 5,352,232 A | 10/1994 | Cohen |
| 5,514,151 A | 5/1996 | Fogarty et al. |

(Continued)

FOREIGN PATENT DOCUMENTS

| | | |
|---|---|---|
| EP | 1388324 | 2/2004 |
| EP | 1955680 | 8/2008 |

(Continued)

*Primary Examiner* — Ryan J Severson
*Assistant Examiner* — Anh Dang
(74) *Attorney, Agent, or Firm* — David J. Johns

(57) ABSTRACT

The present invention relates to methods of using medical cutting tools for treating aortic septal dissections.

4 Claims, 26 Drawing Sheets

(56) References Cited

U.S. PATENT DOCUMENTS

| | | | |
|---|---|---|---|
| 5,584,842 | A | 12/1996 | Fogarty et al. |
| 5,624,455 | A | 4/1997 | Matsuno |
| 5,628,746 | A | 5/1997 | Clayman |
| 5,628,760 | A | 5/1997 | Knoepfler |
| 5,669,922 | A | 9/1997 | Hood |
| 5,683,384 | A | 11/1997 | Gough et al. |
| 5,868,768 | A | 2/1999 | Wicherski et al. |
| 5,993,469 | A | 11/1999 | McKenzie et al. |
| 6,027,514 | A | 2/2000 | Stine et al. |
| 6,165,187 | A | 12/2000 | Reger |
| 7,338,481 | B2 | 3/2008 | Gardeski et al. |
| 2004/0153004 | A1 | 8/2004 | Burbank et al. |
| 2005/0090845 | A1 | 4/2005 | Boyd |
| 2005/0192606 | A1 | 9/2005 | Paul, Jr. et al. |
| 2008/0114364 | A1 | 5/2008 | Goldin et al. |
| 2009/0043259 | A1 | 2/2009 | Hardin et al. |
| 2009/0125044 | A1 | 5/2009 | Lary |
| 2012/0046678 | A1 | 2/2012 | LeMaitre et al. |

FOREIGN PATENT DOCUMENTS

| | | |
|---|---|---|
| FR | 2903292 | 1/2008 |
| WO | 99/30624 | 6/1999 |
| WO | 2007/146194 | 12/2007 |
| WO | 2012/068298 | 5/2012 |

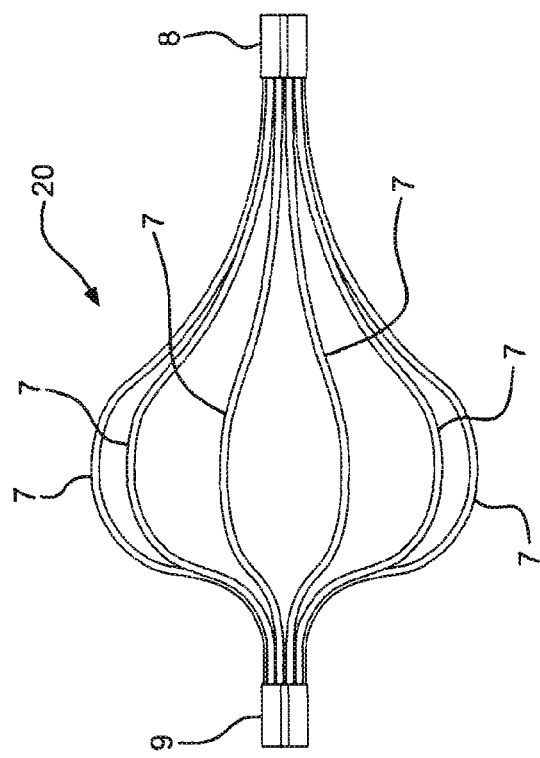
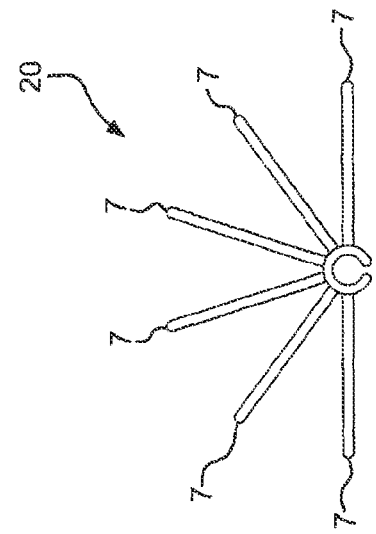
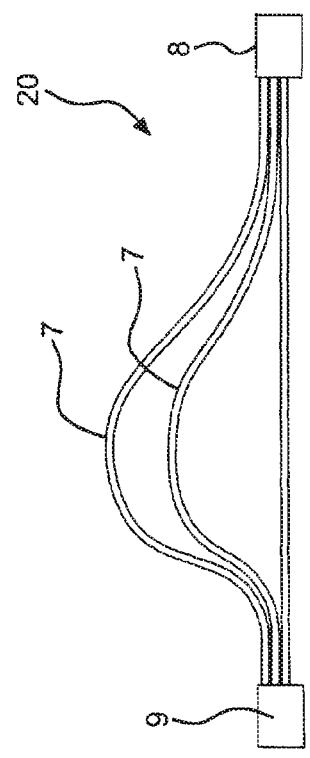
FIG. 11A
FIG. 11B
FIG. 11C

AORTIC DISSECTION SEPTAL CUTTING TOOL

BACKGROUND OF THE INVENTION

Blood vessels of the mammalian body can be subject to a variety of diseases, traumas, and pathological conditions. In some cases, failure of blood vessels is an aspect of one or more of these conditions. Failure of a blood vessel can involve separation of an inner layer of the blood vessel wall from the remaining outer layers of the blood vessel wall. As the inner layer of blood vessel tissue peels away, a space is formed within the layers of the blood vessel tissue. The space usually fills with blood and expands to form two channels, with the peeled-away tissue residing between the two channels. One of the channels is a remnant of the original blood vessel and continues to function as a blood conduit. This anatomical structure is referred to as the true lumen. The blood-filled space delimiting the other channel is referred to as a false lumen. The delamination of tissue in this manner is referred to as a dissection. The tissue residing between the two lumens, or channels, is referred to as the septum. Dissections involving the portion of the aorta that runs through the thoracic cavity are referred to as thoracic aortic dissections. There are two types of thoracic aortic dissections. The first type of thoracic aortic dissection involves the ascending aorta and is referred to as a Type A dissection according to the Stanford aortic dissection classification system. Type A thoracic aortic dissections most often require immediate surgical intervention. The second type of thoracic aortic dissection does not involve the ascending aorta and is referred to as a Type B dissection as classified by the Stanford system. While some Type B dissections require immediate intervention, most can be medically managed for a time before surgery is required. However, damage to the aorta wall due to a dissection can lead to severe complications and/or death.

The ability to treat Type B thoracic aortic dissections surgically is often limited. When surgery is indicated, the principle surgical method currently employed to correct a Type B thoracic aortic dissection is to access the damaged blood vessel surgically and replace the damaged aorta with a vascular graft. One minimally invasive technique currently used is to cut the septum and extend the cut longitudinally along enough of the length of the dissection to disrupt the false lumen. Once the peeled-away tissue "flap" forming the false lumen is surgically disrupted, blood and other fluids contained in the false lumen by the tissue flap can be cleared and denied a location to recollect. The difficulty in performing surgical cuts of this nature inside such a mechanically and biologically compromised aorta, or other major blood vessel, limits the number of suitable candidates for the surgery.

Minimally invasive techniques may provide alternative approaches to treating dissections. One minimally invasive technique utilizes percutaneous transluminal angioplasty balloons to create multiple fenestrations within a septum. This is accomplished by creating a small hole in the septum using a catheter delivered needle or wire. The balloon is then placed in the hole and inflated to enlarge the hole. Another minimally invasive approach uses a wire introduced into an appropriate blood vessel, most commonly in a leg. The wire is inserted into and navigated through the vasculature to the site of the dissection. The wire is advanced through the septum into the false lumen. Once the wire has been advanced down the aorta, some prescribed length, the wire is brought back into the true lumen via the septum. The leading end of the wire is then grasped with an ancillary instrument and pulled down onto tissue of the septum. This places the wire in contact with the septal tissue where the wire functions as a cutting edge. As the wire is pulled, it cuts through the septum. The cut is extended by continuing to pull on the wire. Once a desired cut in the septum is completed, the leading end of the wire is released from the grasping instrument and the wire removed from the vasculature through the introduction site. Controlling movement, direction, and speed of the wire as the wire propagates the incision in the septum is difficult and often limits this procedure to patients with no other surgical options.

A variety of intravascular cutting tools have been developed to treat a number of pathological conditions, none of which include blood vessel dissections. U.S. Pat. No. 3,704, 711, issued to Park, discloses a catheter-based cutting tool for creation of an atrial septal fenestration without thoracotomy. The cutting portion of the tool has a retractable cutting blade confined within a housing. The cutting blade is actuated with a control wire running the length of the catheter. A flexible guidewire is also included with the housing. The flexible guidewire resides above the cutting blade in a retracted configuration and extends to form a loop above the blade when extended. When in an extended configuration, the flexible guidewire is said to provide tactile feedback and assist in locating the cutting tool within a heart. The device may also be sufficiently radiopaque to be visualized with conventional instrumentation. A cut is made in an atrial septum by placing the cutting tool within an atrium with the cutting blade and flexible guidewire in a retracted configuration. Once inside an atrium, the flexible guidewire is extended to form a loop. The loop is used to help a practitioner confirm the location of the cutting tool within an atrium. The flexible guidewire does not assist the cutting blade in contacting or cutting an atrial septum. Once the cutting tool is in a desired location, the control wire is actuated to extend the cutting blade. When the cutting blade has been extended away from its housing, the catheter and housing are withdrawn slightly to bring the cutting blade in contact with septal tissue. As the catheter and housing are withdrawn from an atrium, the extended cutting blade cuts some or all of the atrial septum. Upon completion of a desired septal cut, the cutting blade and flexible guidewire are both retracted into the housing. The housing is then removed from the heart by withdrawing the catheter. If necessary, the procedure can be repeated.

U.S. Pat. No. 5,053,044, issued to Mueller et al., discloses a vascular catheter having a tip with a cutting blade mounted within the tip. The catheter is provided with a mechanism for extending the cutting blade transversely with respect to the catheter when the blade tip is located within a region of stenosis. When the cutting blade is extended, the catheter is moved axially with respect to the catheter so the cutting blade forms an incision in the region of stenosis.

U.S. Pat. No. 5,993,469, issued to McKenzie et al., discloses an arterial catheter system for removing plaque. The catheter system includes an atherectomy assembly. The atherectomy assembly has a mechanism for trapping and holding mobile or fixed plaque and an excising mechanism for removing the plaque. The excising mechanism can include one of several types of rotating cutting blades located within a housing. As the particular cutting blade rotates, plaque protruding into the housing is sheared off and excised from the blood vessel. In some embodiments, rotating cutting blades are provided as single curved blades, cutting blades configured in a twisted helical manner, circular cutting blades, or rotatable cylindrical assemblies having portions removed forming an orifice. As plaque is drawn into the orifice, the cutting blade sweeps across an edge of the orifice opening and excises atheromatous plaque extending through the orifice opening. In another embodiment, a sharpened cylindrical member is initially retained within a housing near an orifice opening to cut plaque. As plaque enters the orifice, the cylindrical cutting blade is advanced toward the distal end of the housing to excise the plaque. In yet another embodiment, a cutting assembly having sharpened movable claws is disclosed. The movable claws are used to enclose, pinch, and cut plaque. Scissor-like cutting blades are also disclosed by McKenzie et al.

McKenzie et al. also disclose an atherectomy catheter equipped with one or more deployable positioning "fingers." According to McKenzie et al., the deployable positioning fingers act to bias the catheter in the lumen of a blood vessel toward a plaque within a region of interest. The positioning fingers may be mechanically expandable projections or inflatable balloons. The inflatable balloons are said to be inflatable through one or more lumens within the catheter.

None of these devices are designed or intended to treat dissections in vascular structures. Indeed, none of these devices are able to reliably locate and disrupt vascular dissections. A medical cutting tool for treating dissections in vascular structures would require a delivery catheter-based cutting blade assembly with a remotely movable cutting blade combined with one or more expandable displacement elements assisting the placement, contact, support, and operation of the cutting blade. If a procedure were to be implemented to treat dissections involving the creation of a hole in the septum by inserting a medical cutting tool through the hole, a member could be added to the cutting tool to blunt the assembly and assist in locating the assembly in the false lumen. In such a procedure, the cutting tool would be used to cut enough of the dissection to reduce or eliminate the false lumen. In some instances, a prosthetic medical device might be used following the disruption of the septum.

SUMMARY OF THE INVENTION

The present invention relates to medical devices for treating dissections, particularly dissections in vascular structures. The invention also relates to systems for delivering and activating the medical devices.

As described above, dissections cause formation of a false lumen in a blood vessel, or other anatomical structure, from tissue defining a true lumen. One approach to treating dissections is cutting the septum to open the false lumen. Opening the false lumen permits any contents of the lumen to be removed. A severed septum also limits or prevents further collection of fluid, such as blood, in the false lumen. The present invention readily accesses, engages, and controllably cuts tissue of a dissection with little or no damage or trauma to adjacent tissues and anatomical structures.

The present invention has a cutting blade assembly for engaging septal tissue separating a false lumen from a true lumen in a dissection. The cutting blade assembly has at least one cutting blade held by a movable housing. The movable housing is remotely actuated with an elongate member. The elongate member usually runs the length of a delivery catheter and terminates with a control knob, handle, or hub. In some embodiments, a flexible housing member is attached to the cutting blade assembly. When the cutting blade assembly portion of the invention is positioned in proximity to tissue of a septum in a dissection, the invention can be manipulated to introduce the flexible housing member into the false lumen. Once the flexible housing member is located in a false lumen, the cutting blade is brought into contact with the septal tissue. A guidewire, or "navigation wire," is often used to assist in locating an entrance to a false lumen and introducing the flexible housing member into the false lumen. The guidewire also helps assure the present invention remains properly positioned in one or both lumens.

The present invention also has at least one expandable displacement element positioned on a delivery catheter near the cutting blade assembly. The expandable displacement element assists in locating and maintaining the invention at the desired site. In addition, it provides tactile feedback and visual reference to a practitioner. When the invention is positioned at a desired location, the expandable displacement element exerts force against tissue defining a lumen. As the expandable displacement element touches and presses against luminal tissue, the cutting blade assembly contacts and engages tissue of a septum in a dissection. As the movable cutting blade housing is actuated, the expandable displacement element assists in maintaining the cutting blade in contact with tissue of a septum in a dissection as the tissue is cut, or otherwise disrupted, with the cutting blade. The displacement element also limits movement of the delivery catheter during a cutting procedure. Limiting the movement of the delivery catheter allows for more precise cuts to be made in a septum.

Once a cutting procedure is completed, the movable cutting blade housing is moved to a location on the delivery catheter where the expandable displacement element can collapse, or otherwise alter its shape, and allow the cutting blade assembly to be retrieved from the treatment site.

In some embodiments, an extension is included with the cutting blade assembly. In addition to providing additional tactile feedback and visual reference to a practitioner during a procedure, the extension can also limit or prevent placement of the invention at an undesired location. In some embodiments, the extension has a hollow portion in which a wire, or other elongate member, can be inserted. The extension can be a generally linear-shaped element. In other embodiments, the extension can have a curved, or other non-linear, shape. A curved extension can be hollow and provide a route through which a navigation wire, or other elongate element, can be threaded.

In some embodiments, a delivery catheter is provided for the cutting blade assembly and expandable displacement elements. The delivery catheter can have more than one channel, or luminal space, running all, or part, of the length of the catheter. In most embodiments, at least one channel of the delivery catheter contains an elongate member used to remotely actuate the movable housing component of the cutting blade assembly. Other channels of the delivery catheter can be used for guide wires or other devices.

A hub is often placed on an end of the delivery catheter opposite the cutting blade assembly and expandable displacement element. The hub can include access ports for a guidewire or introduction of fluids or other devices.

Accordingly, one embodiment of the present invention relates to a method of treating an aortic dissection comprising providing a catheter having at least one displacement element attached to said delivery catheter, at least one cutting edge incorporated with said catheter, said cutting edge being actuated with an elongate member, and a housing for said cutting edge attached to said catheter, placing said catheter within an arterial system, advancing said catheter through said arterial system to a location proximal to a primary entry tear of said aortic dissection, contacting aortic tissue with said displacement element, cannulating a guidewire from said catheter through said entry tear of said aortic dissection into a false lumen delimited by a septum, engaging said at least one cutting edge with said septum; and advancing said cutting edge through said septum.

Another embodiment of the present invention relates to a method of treating an aortic dissection comprising, providing a catheter having at least one displacement element attached to said delivery catheter, at least one cutting edge incorporated with said catheter, said cutting edge being actuated with an elongate member, and a housing for said cutting edge attached to said catheter, placing said catheter within an arterial system, advancing said catheter through said arterial system to a location distal to a primary entry tear of said aortic dissection, contacting aortic tissue with said displacement element, forming a hole in septal tissue of said aortic dissection, cannulating a guidewire from said catheter through said hole in tissue of said aortic dissection into a false lumen delimited by said septal tissue, engaging said at least one cutting edge with said septum, and advancing said cutting edge along said septum.

Thus, in accordance with the principles of the invention, there is provided apparatus and methods for treating dissections in aortic and other tissue. The scope of the invention is limited, however, only through the claims appended hereto.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 11A illustrates a top view of a displacement element assembly of the present invention.

FIG. 11B illustrates an end-on view of a displacement element assembly of the present invention.

FIG. 11C illustrates a side view of a displacement element assembly of the present invention.

DETAILED DESCRIPTION OF THE INVENTION

The present invention relates to cutting tools useful in medical applications. The cutting tools are usually combined with a delivery device. In many embodiments, the delivery device also includes components for influencing the placement and controlling the operation of the cutting tools. The cutting tools of the present invention are most often used inside a living body.

A preferred embodiment of the present invention includes a cutting blade assembly having at least one movable, or translatable, cutting blade incorporated in the assembly. A translatable cutting blade changes location in space without rotation. Actuation of the movable blade is effected remotely. At least one displacement element is provided to assist in positioning and operating the movable cutting blade. In some embodiments, the at least one displacement element is self-expanding. In preferred embodiments, extensions are provided to limit or prevent placement of the invention in an undesired location. Often a delivery catheter is employed in the present invention having two or more channels, or luminal spaces, within the catheter. With multi-lumen catheters, one channel is used to attach the cutting blade assembly to the catheter. An elongate member is attached to the movable cutting blade portion of the cutting blade assembly and used to actuate the movable cutting blade. In some embodiments, the elongate member is hollow and allows introduction of a guidewire, or other device, up to and in some embodiments through the movable cutting blade assembly. In some of these embodiments, the guidewire can extend beyond the cutting blade assembly. If one or more hollow extensions are present, the guidewire can be threaded through the extension. In embodiments having a hollow flexible housing member attached to the delivery catheter, the guidewire can be threaded from the extension into the hollow portion of the flexible housing member. In embodiments having a flexible housing member, the housing member contains at least a portion of the movable cutting blade. The flexible housing member also serves to assist in locating a false lumen and maintaining the cutting blade in contact with tissue. When multi-lumen delivery catheters are used, one of the remaining channels in a multi-lumen delivery catheter is often used for an additional guidewire.

A procedure for using the present invention is illustrated in FIGS. 1-6. In these Figures, the letter "A" refers to an aorta and the letter "S" refers to a septum, or septal tissue. The letters "TL" refer to a true lumen and the letters "FL" refer to a false lumen. The letters "PT" refer to a primary tear in the aorta.

Figure 1:
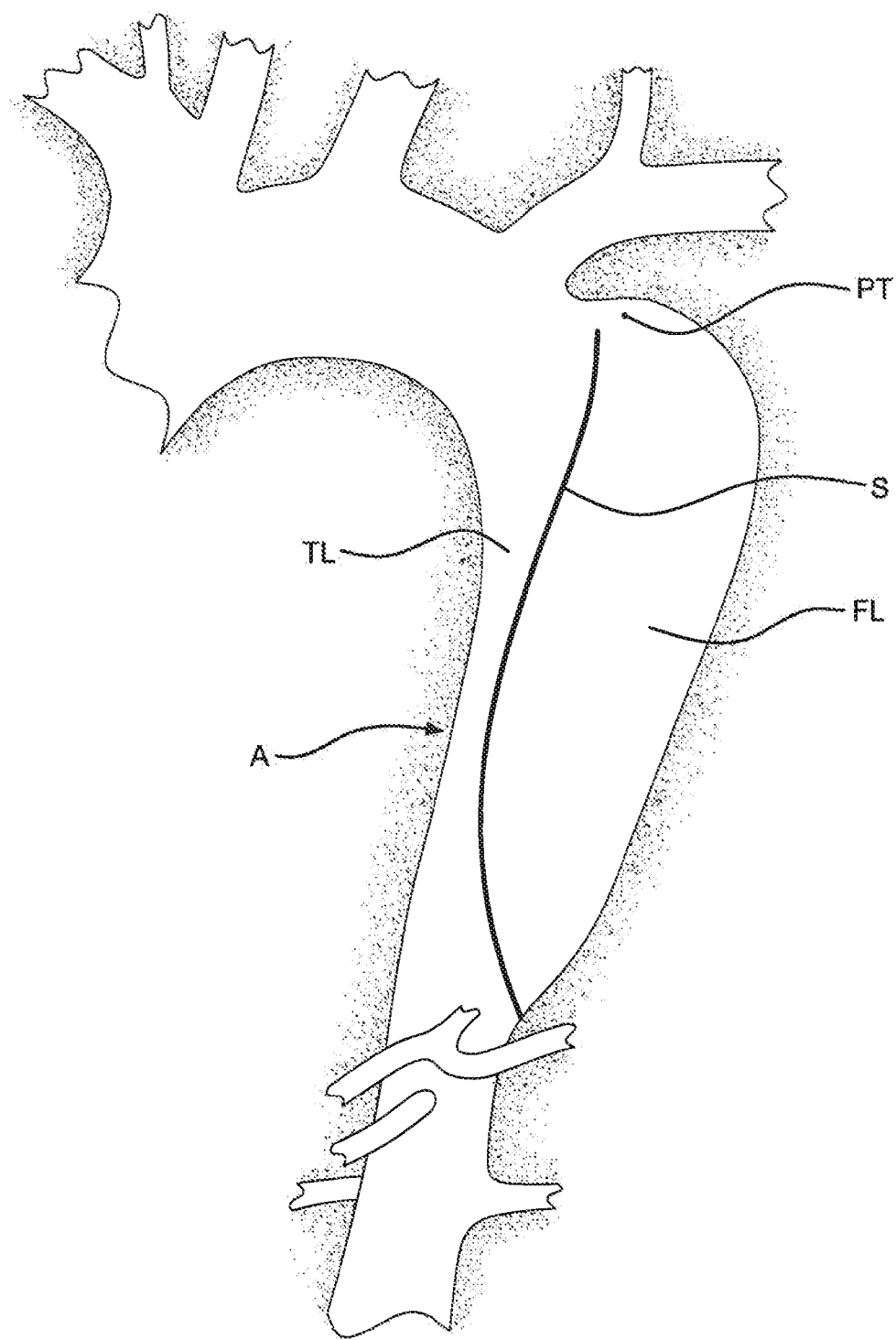
FIG. 1 Illustrates a cross-section of a Type B Aortic Dissection
Figure 2:
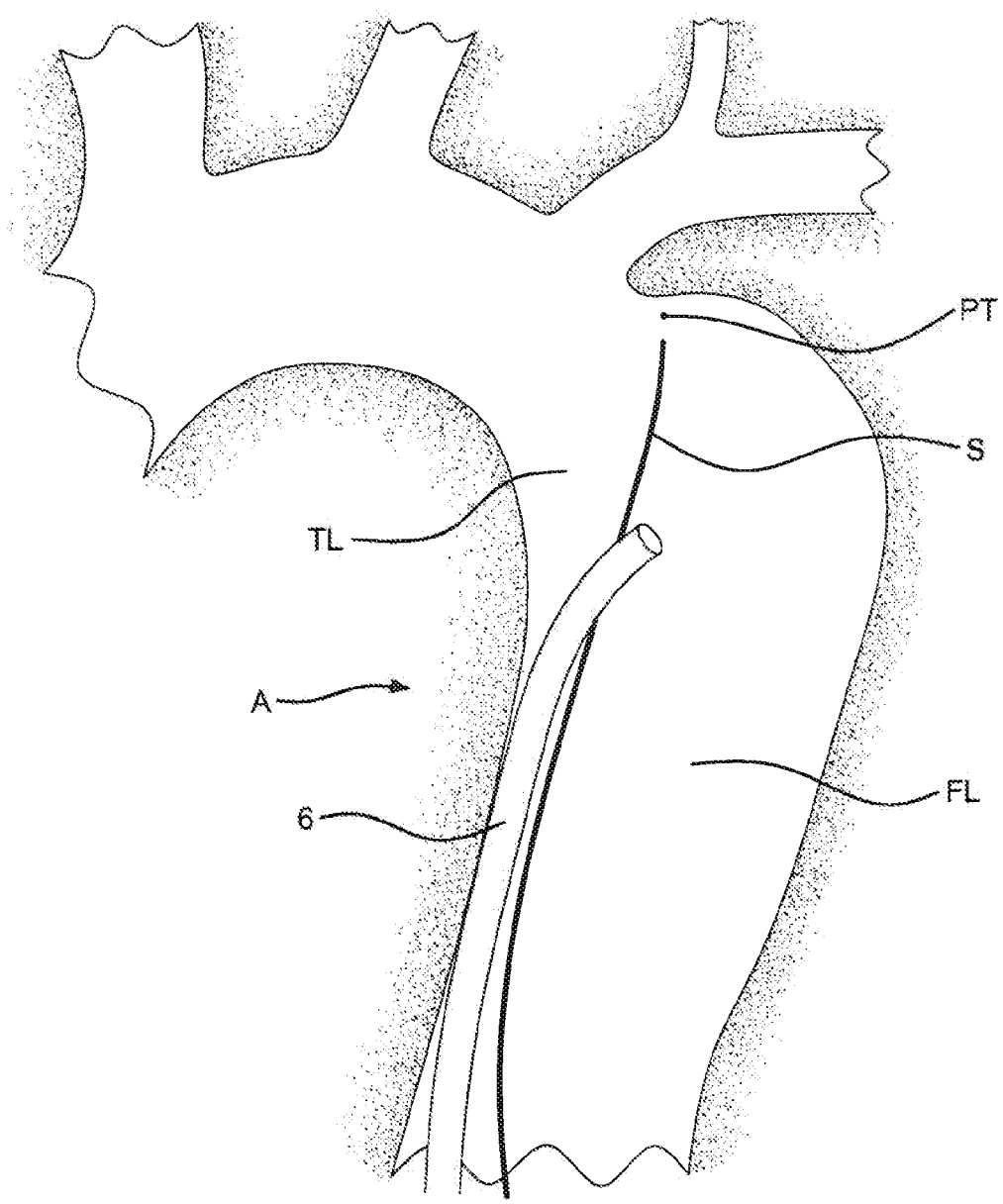
FIG. 2 Illustrates the puncture and crossing of the septum with a sheath
Figure 3:
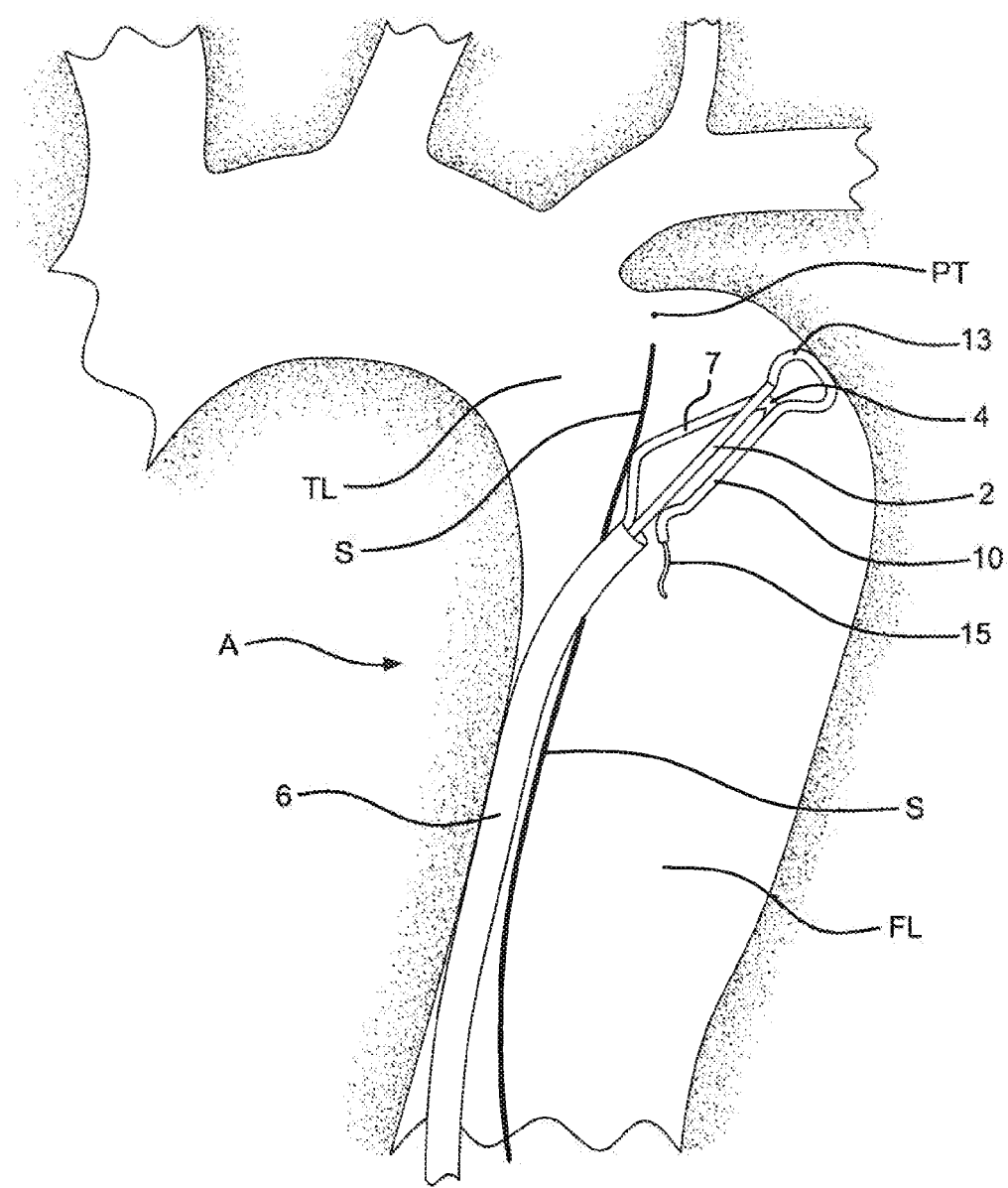
FIG. 3 Illustrates deployment of the cutting tool in the false lumen
Figure 4:
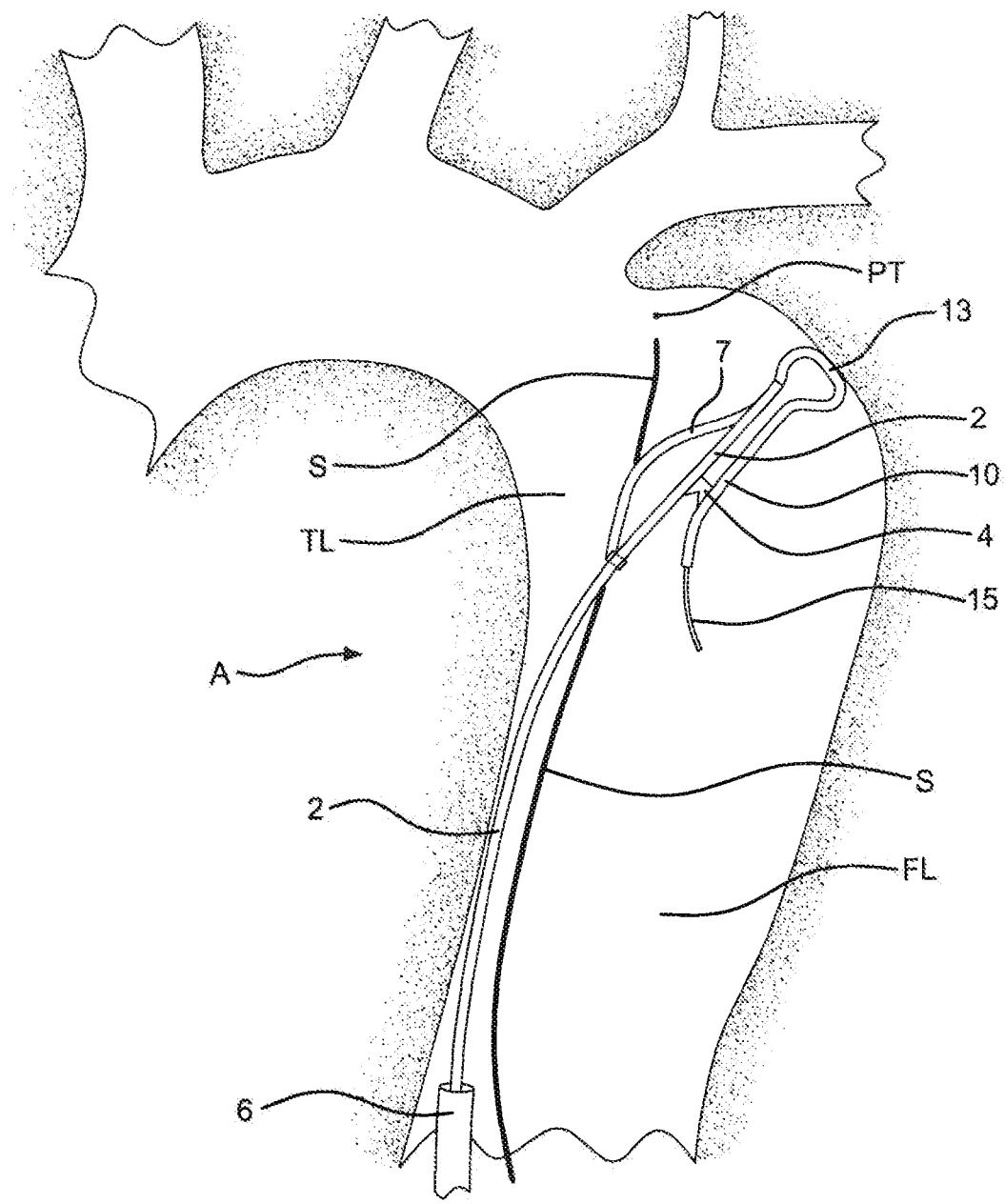
FIG. 4 Illustrates the cutting tool with blade activated
Figure 5:
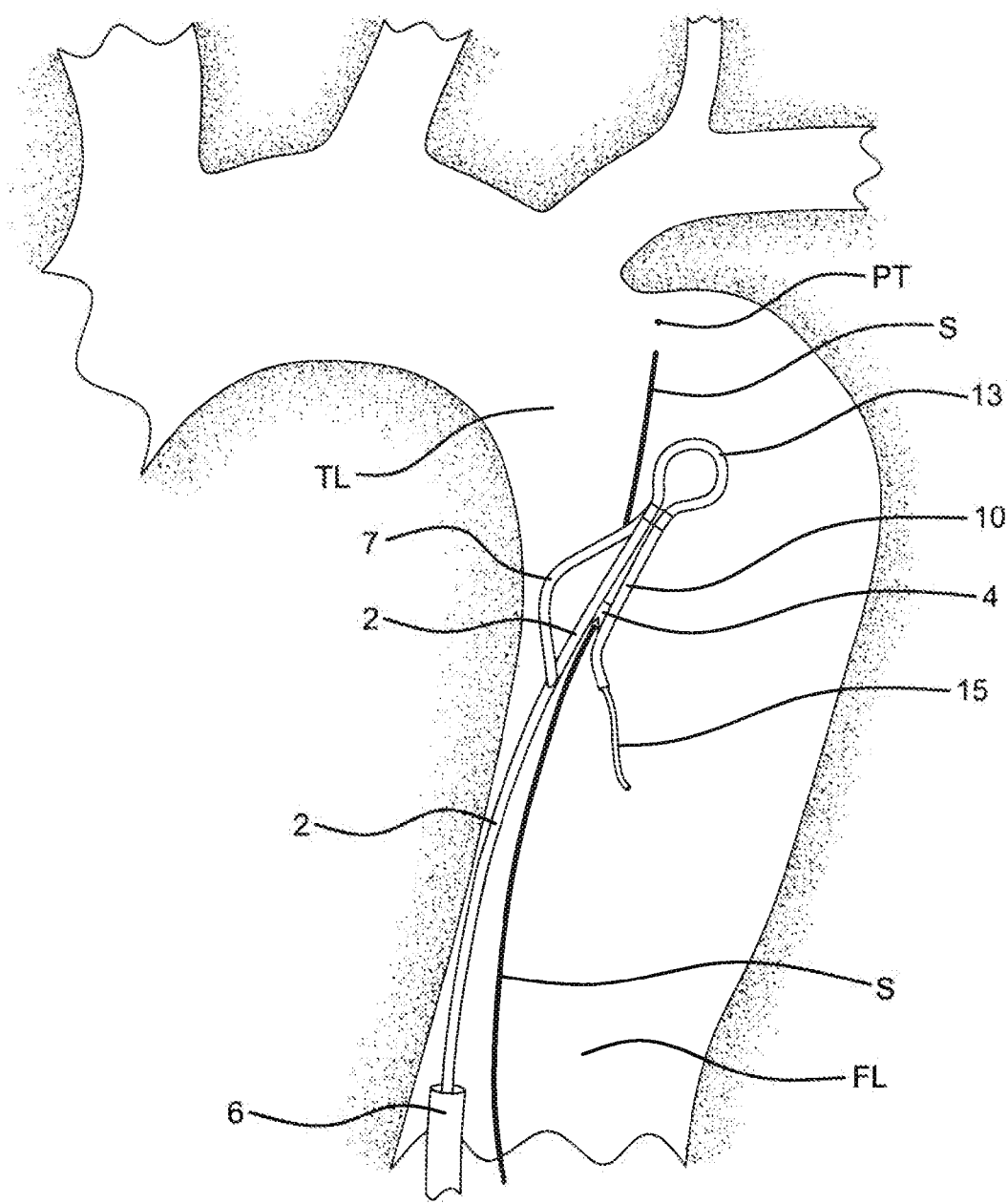
FIG. 5 Illustrates the cutting tool being retracted to engage the septum
Figure 6:
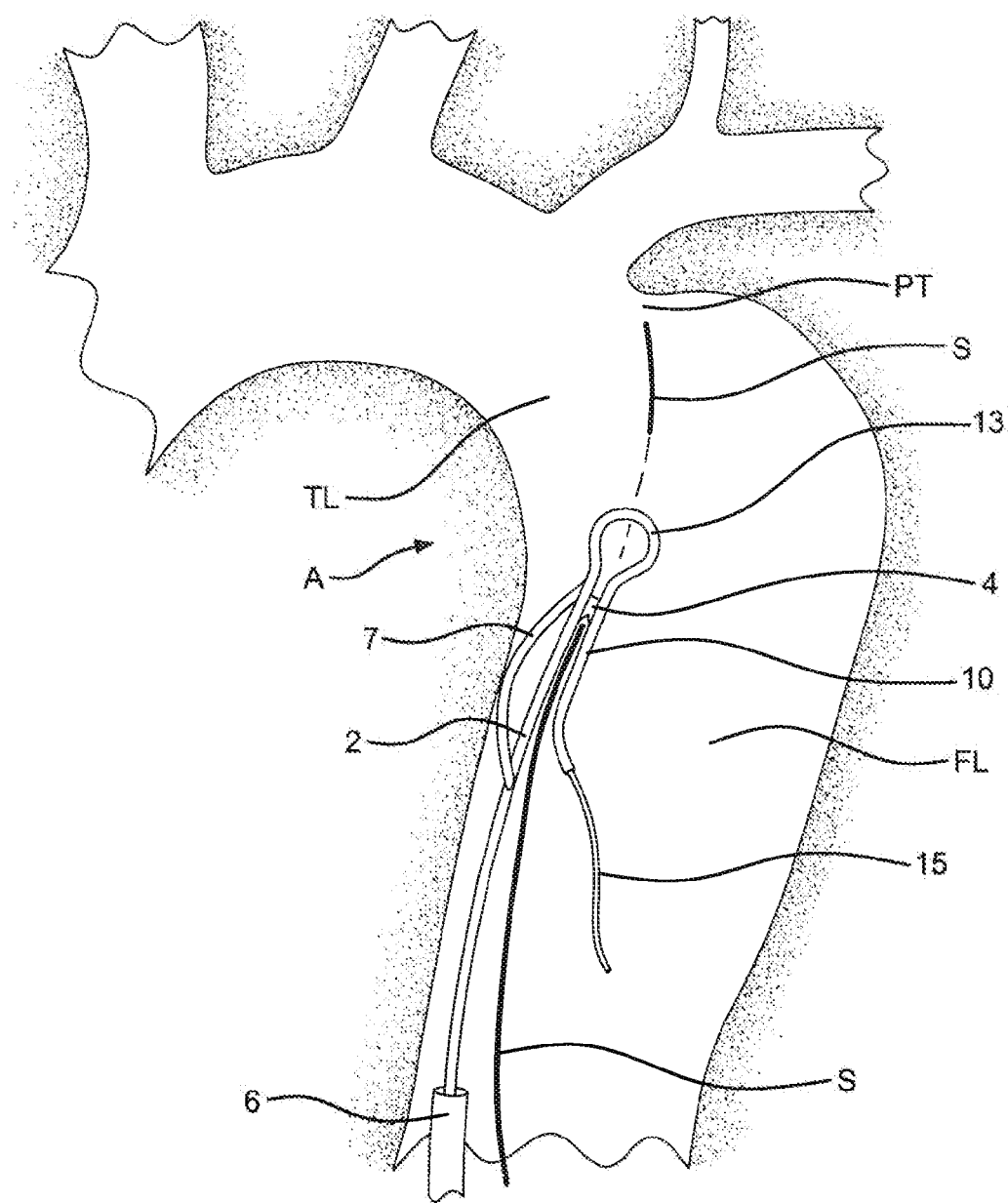
FIG. 6 Illustrates the cutting of the septal tissue.

FIG. 1 illustrates a cross-sectional view of an aorta "A" having a dissection in need of treatment. As shown in FIG. 2, a tubular sheath (6) for housing and delivering a cutting assembly of the present invention is advanced from the true lumen "TL" across septum "S" into false lumen "FL." Prior to advancing the sheath (6) through the aorta "A," a suitably sized and shaped hole was made or found existing in the septum "S" (not shown). FIG. 3 illustrates a cutting tool of the present invention having been advanced from within the sheath (6) into the false lumen "FL." Once properly positioned in the false lumen "FL," with the aid of at least one displacement element (7), the sheath (6) is retracted to a desired location (FIG. 4). FIG. 5 illustrates cutting blade (4) cutting the septum "S." Once the cutting blade (4) is brought into contact with the septum "S," the cutting blade is then remotely retracted, translated, or otherwise moved to cut the septum "S." The at least one displacement element (7) aids in maintaining the cutting blade (4) against the septum "S." FIG. 6 illustrates a completed cut in the septum "S." At this stage in the cutting process, cutting blade (4) is retracted to same or substantially the same position it was in at the beginning of the cutting process. The at least one displacement element (7) is illustrated pressing against the side of the aorta substantially opposite the cutting blade assembly.

In a preferred embodiment, a flexible polymeric delivery catheter having two channels, or luminal spaces, running the length of the catheter is used. A locking mechanism for a control hub assembly is attached to one end of the delivery catheter by gluing or other suitable method. Preferred locking mechanisms have helical threads to enable a control hub having helical threads to be screwed onto the locking mechanism. In the finished device, a control hub having at least one opening is attached to the locking mechanism. The opening in the control hub allows an elongate member residing within the delivery catheter to exit the catheter. In embodiments with more than one elongate member residing within the delivery catheter, one elongate member is configured to move within the delivery catheter. The movable elongate member is used to remotely actuate a movable cutting blade. The end of the delivery catheter having a locking mechanism remains outside a patient during use of the invention. This end of the delivery catheter is referred to herein as the proximal end. A cutting blade assembly is attached to the opposite end of the delivery catheter, referred to herein as the distal end of the delivery catheter.

Figure 7:
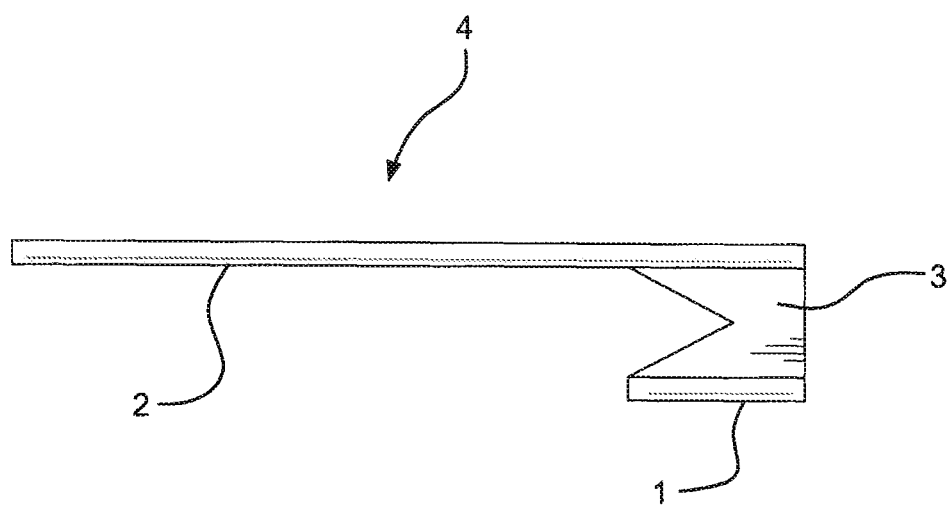
FIG. 7 illustrates a cutting blade assembly of the present invention.

A cutting blade assembly and a displacement element assembly are attached to the distal end of the delivery catheter. A cutting blade assembly is illustrated in FIG. 7. The cutting blade assembly (5) has a cutting blade (4) with an appropriately shaped cutting edge formed in the blade. A blade housing (3) is attached to a non-cutting side of the cutting blade by forming a suitably dimensioned notch in the blade housing to receive and retain a non-cutting edge of the cutting blade (4). The blade housing (3) is attached as shown in FIG. 7.

An elongate member (2) is attached to a non-cutting side of the cutting blade by forming a suitably dimensioned notch in the elongate member (2) to receive and retain an opposite non-cutting edge of the cutting blade (4). The elongate member (2) is attached as shown in FIG. 7. The opposite end of the elongate member is referred to herein as the free end. The elongate member (2) is several centimeters longer than the delivery catheter (6) in which it resides. The free end of the elongate member (2) is introduced into one of the channels, or luminal spaces, of the delivery catheter at the distal end. The elongate member is threaded through the channel of the delivery catheter until the free end emerges from the proximal end of the delivery catheter.

Prior to introduction of the elongate member (2) component of the cutting blade assembly (5) into a channel of the delivery catheter (6), a suitably dimensioned notch (30) is formed in the distal end of the delivery catheter (FIG. 7). The notch (30) permits the cutting blade (4) component of the cutting blade assembly (5) to translate or otherwise move in a linear direction without rotation of the cutting blade (4). The free end of the elongate member (2) is advanced through the delivery catheter (6) to a point where the translatable cutting blade (4) resides within the notch (30).

A displacement element assembly (20) is then attached to the delivery catheter (6). The displacement element assembly (20) is made of a flexible material. The flexible material can be metallic and/or polymeric. A preferred flexible metallic material has shape-memory properties and is capable of self-expanding from a confined configuration to an unconfined configuration with its own stored energy. The flexible material is usually in the form of at least one strip. The at least one flexible strip (7) is attached to, or includes, at least one movable collar (8 or 9).

In some embodiments, a displacement element assembly (20) has a collar (8, 9) at each end of the assembly (FIGS. 11A, 11C). Each collar has a suitably dimensioned notch formed in the collar (FIG. 11A). The notches are aligned with one another (FIG. 11A). When the displacement element assembly is placed on a delivery catheter (6), the notch in the first collar (e.g., 9) to be placed on the delivery catheter (6) permits the collar to pass the cutting blade (4) projecting from the delivery catheter (6). The other collar (e.g., 8) is then placed over the delivery catheter (6). The first collar (e.g., 9) to be placed on the delivery catheter (6) is attached, or otherwise fixed, to the delivery catheter at a location on the delivery catheter (6) that may permit the movable cutting blade (4) to contact and move the collar (e.g., 8) located at the opposite end of the displacement element assembly (20). In other embodiments, the collar is attached, or otherwise fixed, to the delivery catheter at locations or in configurations that permit the collar to move independently of the cutting blade.

In embodiments having a displacement element assembly (20) with at least one displacement element (7) attached at one end to a single collar (8 or 9) and the other end of the displacement element unattached, or free, the collar of the displacement element assembly (8 or 9) is usually placed over the delivery catheter (6) after the cutting blade assembly (5) is combined with the delivery catheter (6). The free end of the at least one displacement element (7) is then attached to the delivery catheter (6) with adhesive, heat shrink tubing, or other suitable material at a location on the delivery catheter (6) that permits the movable cutting blade (4) to contact and move the collar (e.g., 8) located at the opposite end of the displacement element assembly (20). In other embodiments, the collar is attached, or otherwise fixed, to the delivery catheter at locations or in configurations that permit the collar to move independently of the cutting blade.

Figure 9:
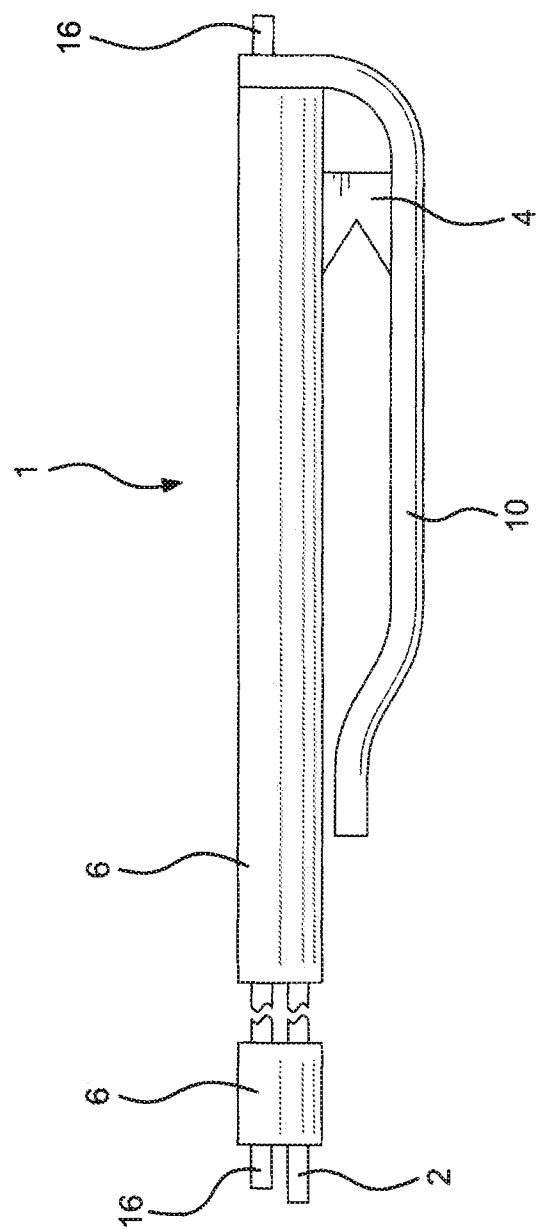
FIG. 9 illustrates a cutting blade assembly, an accompanying delivery catheter, an optional guidewire, and a flexible housing member.

In a preferred embodiment, a flexible housing member (10) is attached to the delivery catheter (6) is illustrated in FIG. 9. At least a portion of the flexible housing member is hollow and sized to contain and retain blade housing (3). In this configuration, the flexible housing member protects tissue from the cutting blade until the cutting blade is positioned and actuated. A notch, or slit, is usually cut in the flexible housing member (10) to permit the movable cutting blade (4) to translate, or otherwise move without rotation of the cutting blade (4). In preferred embodiments, the opposite end of the flexible housing member (10) is bent as illustrated in FIG. 9. The bent end of the flexible housing member contacts (not shown) or nearly contacts the delivery catheter (6) (FIG. 9). In addition to shielding the cutting blade until use and assisting in placement of the cutting blade assembly, the flexible housing member facilitates atraumatic removal of the device from the anatomy. As discussed in greater detail, infra, the blade housing (3) and flexible housing member (10) can be hollow and dimensioned to accommodate a guidewire (15).

Figure 10:
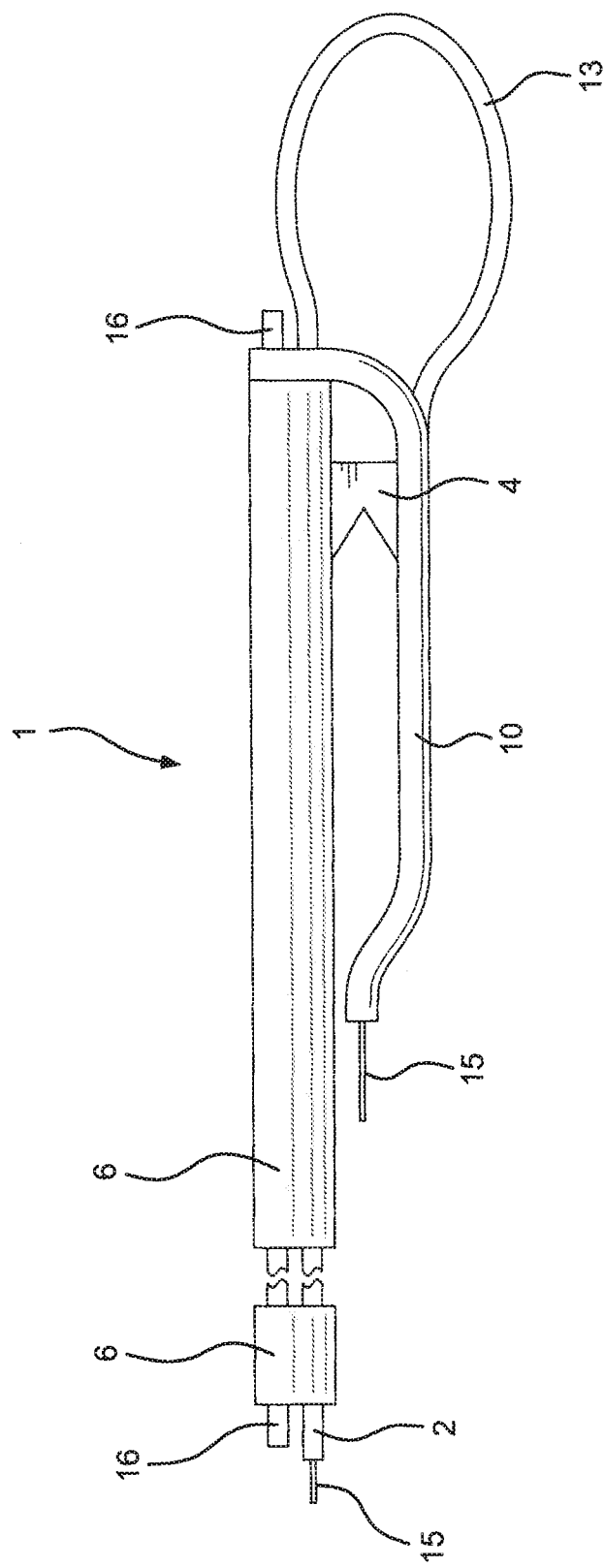
FIG. 10 illustrates a cutting blade assembly, an accompanying delivery catheter, an optional guidewire, a flexible housing member, and a housing wire.

As illustrated in FIG. 10, an extension (13) in the form of a flexible hollow tube is attached at one end to elongate member (2). The other end of extension (13) is attached to flexible housing member (10). This configuration provides a continuous path through elongate member (2), extension (13), and flexible housing member (10). In addition to assisting in the location and operation of the cutting blade assembly, the extension also forms an atraumatic tip. The atraumatic tip helps prevent, or limit, propagation of the dissection in a retrograde direction. The continuous path can be used to contain and direct a guidewire (15). The guidewire (15) can assist in locating a false lumen and guiding flexible housing member (10) into the false lumen.

Figure 12:
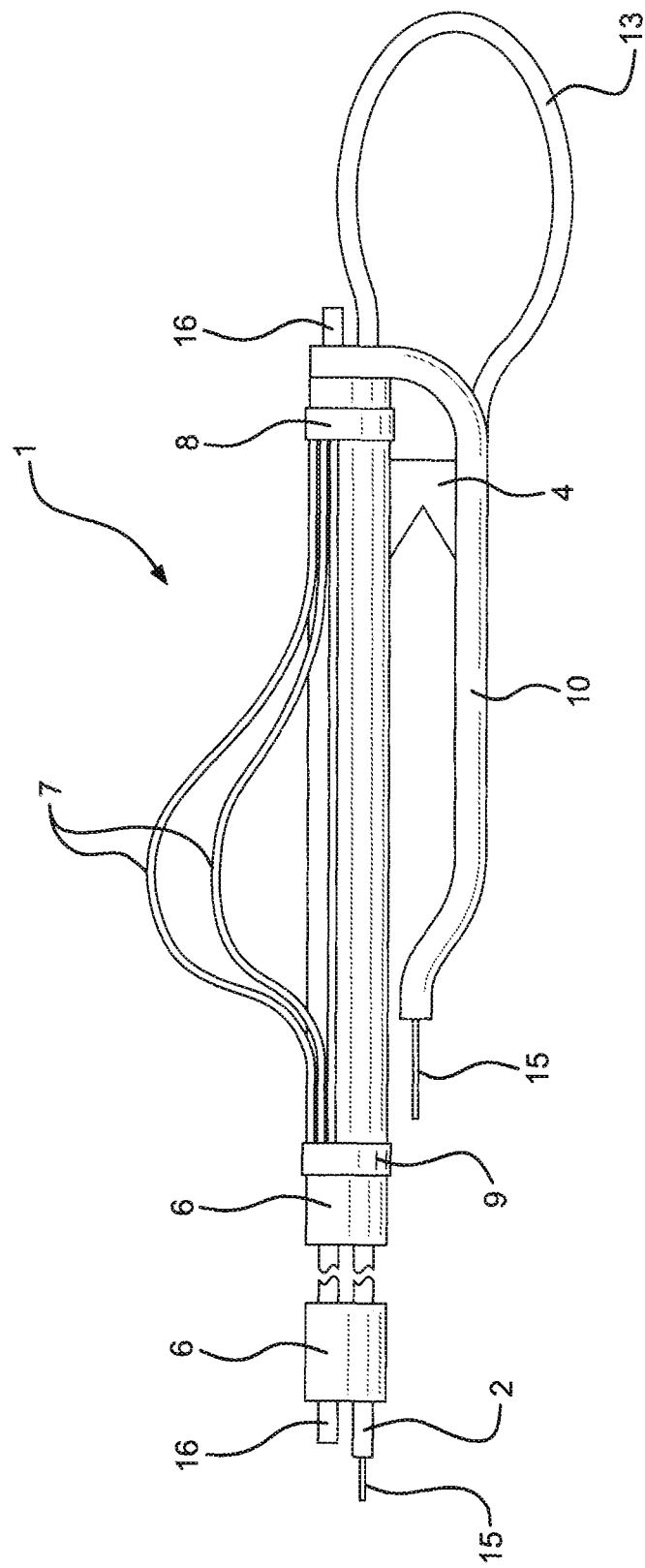
FIG. 12 illustrates an embodiment of the present invention.
Figure 13:
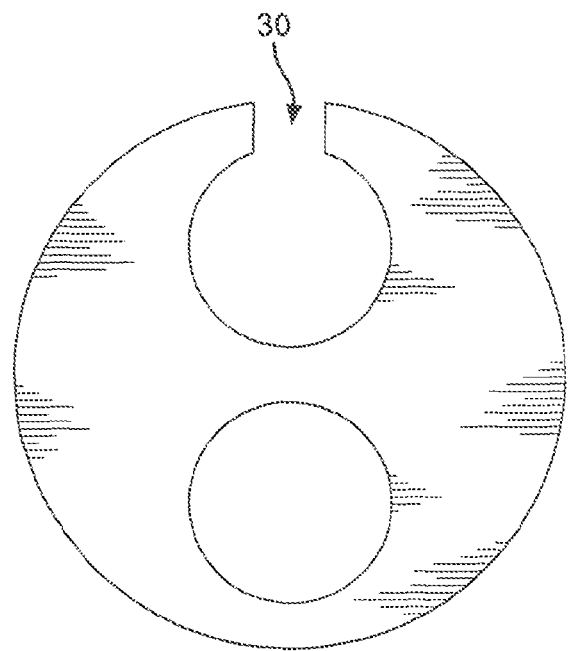
FIG. 13 illustrates a cross-section of a delivery catheter having two channels, or lumens, therein.

In a preferred embodiment, an available channel, or luminal space, in a multi-lumen delivery catheter (6) can be used for a second guidewire (16), or other device (FIG. 12).

In practice, the cutting blade assembly is introduced into a patient having a pathological dissection in need of treatment. The introduction of the cutting blade assembly can be facilitated with a guidewire (16). In one method, a hole or other opening, is made in septal tissue separating a true lumen from a false lumen. The cutting blade assembly is then inserted through the hole until the cutting edge of the movable cutting blade is in contact, or near contact, with septal tissue. In embodiments having an extension, the extension can contact surfaces of the false lumen and limit or prevent introduction of the cutting blade assembly into the false lumen beyond a desired location. The extension can provide tactile feedback to a practitioner. The extension can also be visualized in vivo with appropriate techniques and equipment.

As the movable cutting blade portion of the cutting blade assembly is placed at or near septal tissue identified for cutting, the displacement element(s) expand and press against tissue. As the displacement element(s) press against tissue, the movable cutting blade is urged into contact with septal tissue to be cut. As septal tissue is cut with the movable cutting blade, the displacement element(s) continue to press against tissue and help maintain the cutting blade in contact with septal tissue as additional septal tissue is cut.

To cut septal tissue, the elongate member (2) is pulled upon by a practitioner to engage the cutting edge of the movable cutting blade with the septal tissue and advance the cutting blade through enough septal tissue to treat the dissection. In preferred embodiments, the cutting blade translates, or otherwise moves without rotation of the cutting blade, as the cutting blade (4) is moved by the elongate member (2). In some situations, it may be necessary to pull on the delivery catheter, rather than, or in addition to, the elongate member to cut the septal tissue.

Once the septal tissue has been cut, the elongate member (2) is pushed to move the cutting blade toward the distal end of the delivery catheter. As the cutting blade is so moved, or retracted, the cutting blade (4) contacts and moves movable collar (8) toward the distal end of the delivery catheter (6). As the movable collar (8) is so moved, the displacement element(s) are altered to an unexpanded, or less expanded, configuration. In addition, the flexible housing member (10) returns to a position in contact, or nearly in contact, with the delivery catheter (6). Once the displacement element(s) are in an unexpanded, or less expanded, configuration, and the flexible housing returned to its original location, the cutting blade assembly can be removed from the treatment site by withdrawing the delivery catheter. The displacement element can also be collapsed by allowing the collar to slide unaided toward the distal end of the delivery catheter during removal.

Figure 15:
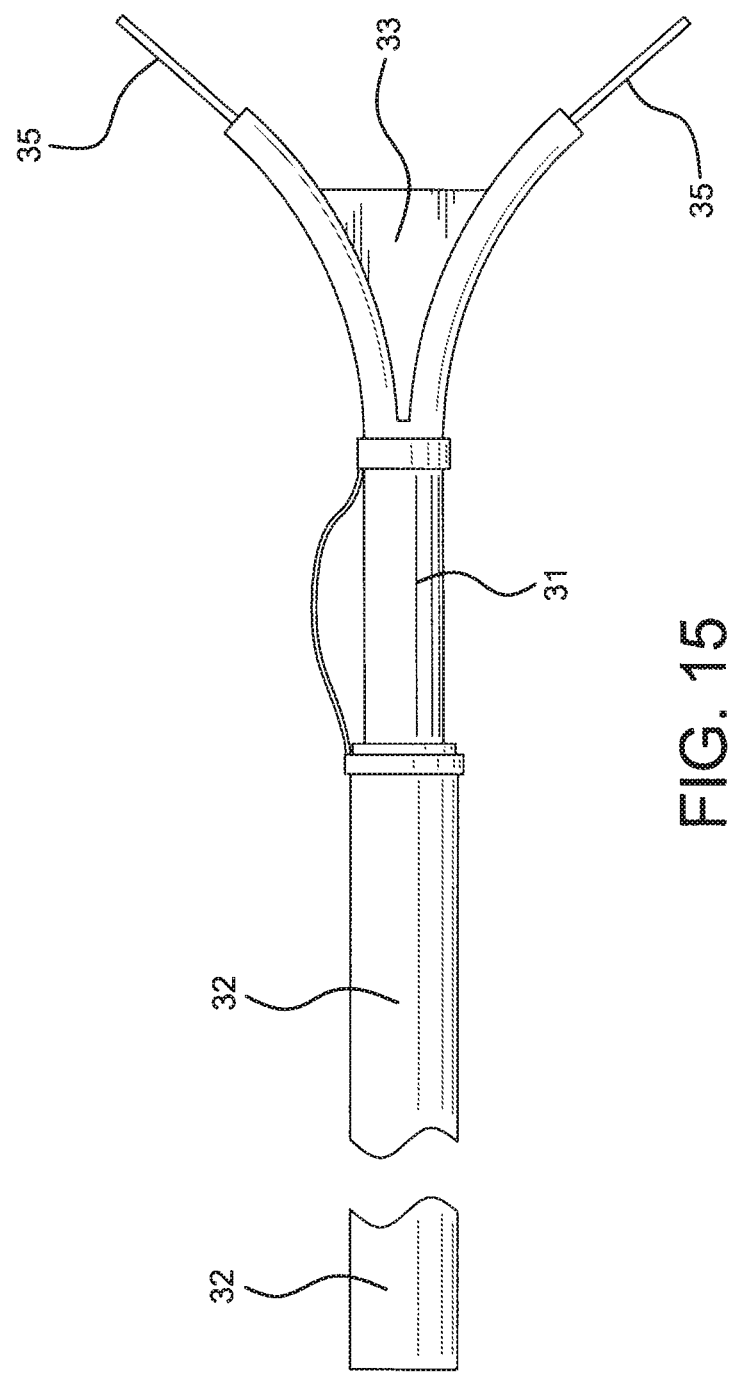
FIG. 15 illustrates an embodiment of the present invention.

In another embodiment of the present invention, a stationary cutting blade is utilized (FIG. 15). In this embodiment, two guidewires are used to position the device at a desired location. Once in place, one guidewire resides is the true lumen, while the other guidewire resides in the false lumen. At least one displacement element is provided to assist in positioning the cutting blade at a desired location and maintaining the cutting blade in contact with tissue.

Figure 16:
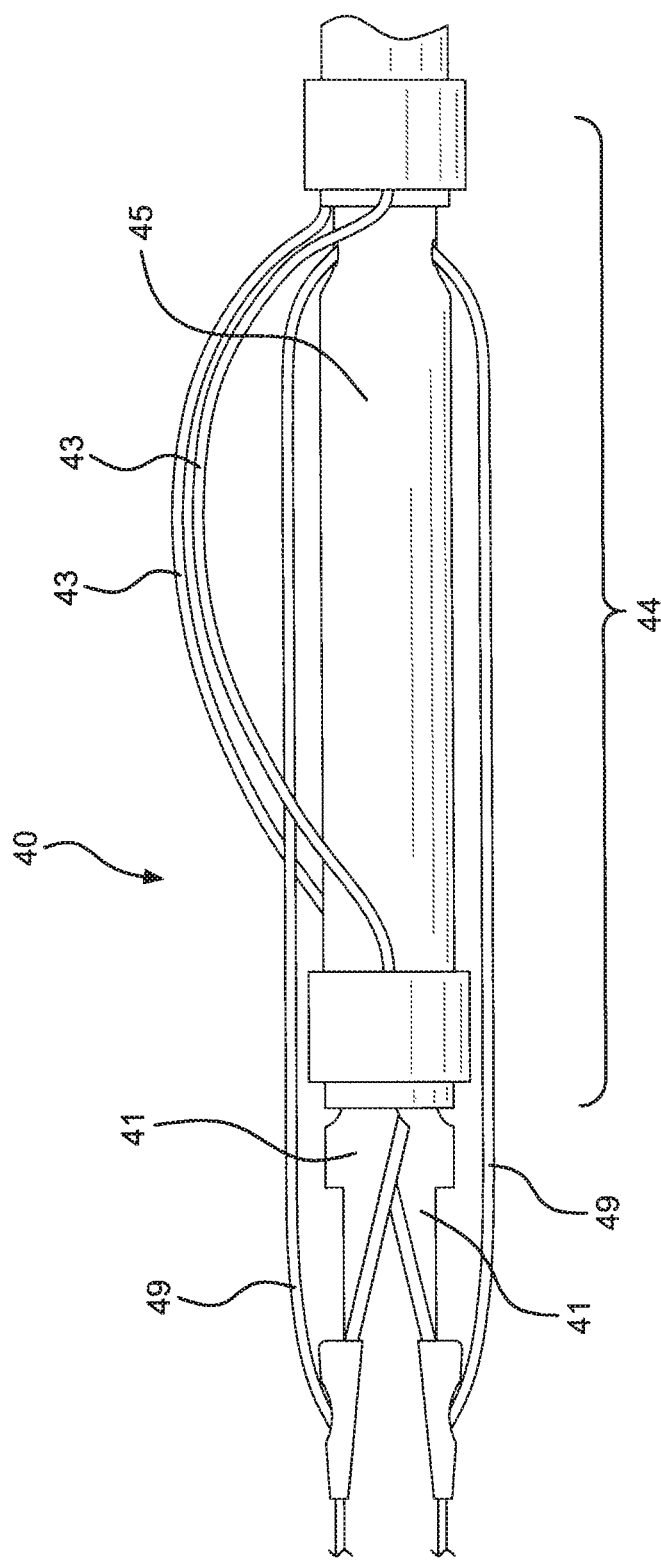
FIG. 16 illustrates an embodiment of the present invention.

Another embodiment of the present invention is illustrated in FIG. 16. This embodiment has remotely movable cutting blades. The movable cutting blades are arranged to provide a scissor-like cutting action. This embodiment is also provided with at least one displacement element.

In another embodiment of the present invention, a serrated cutting wire is provided in a delivery catheter or sheath. A preferred embodiment has a motorized device attached to the cutting wire. The motorized device is configured to move the cutting wire back and forth. This embodiment is also provided with at least one displacement element.

Figure 26:
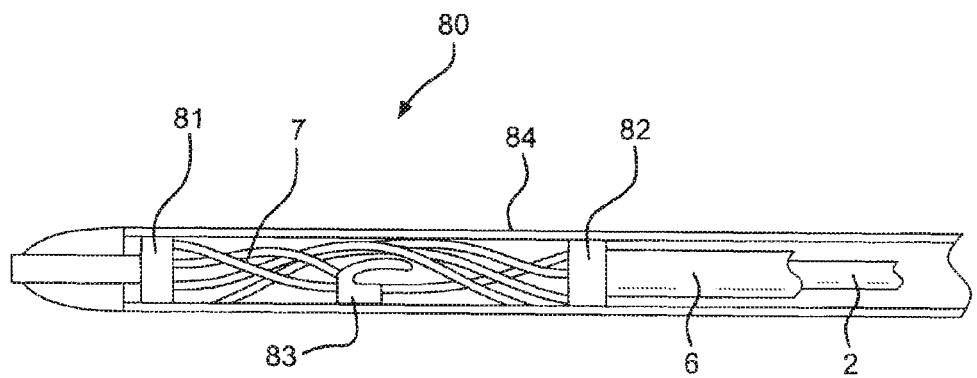
FIG. 26 illustrates an embodiment of the present invention.
Figure 27:
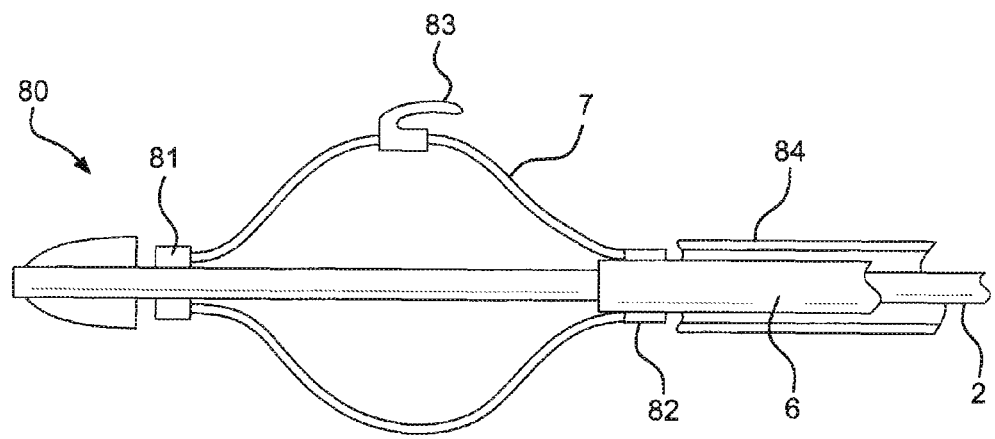
FIG. 27 illustrates an embodiment of the present invention.
Figure 28:
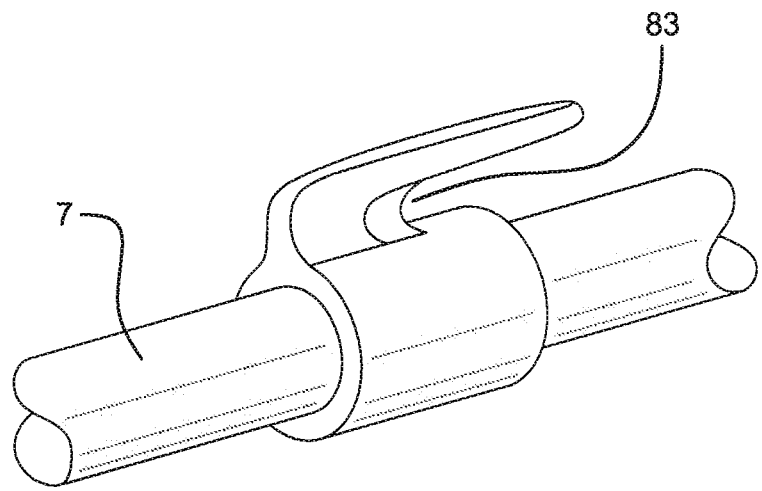
FIG. 28 illustrates an embodiment of the present invention.

Another embodiment of the present invention is illustrated in FIGS. 26-28. This embodiment has a plurality of displacement elements having the general shape of a wire basket. At least one cutting blade, hook, or other cutting edge is attached to at least one displacement element.

Figure 30:
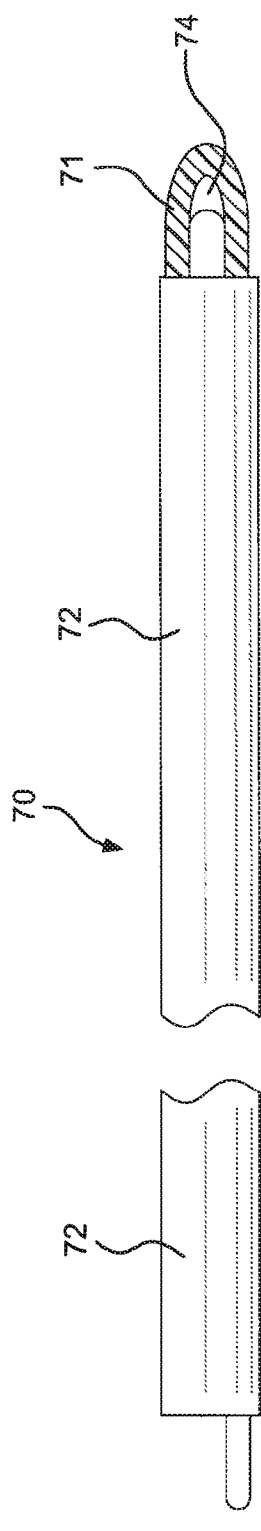
FIG. 30 illustrates an embodiment of the present invention.
Figure 31:
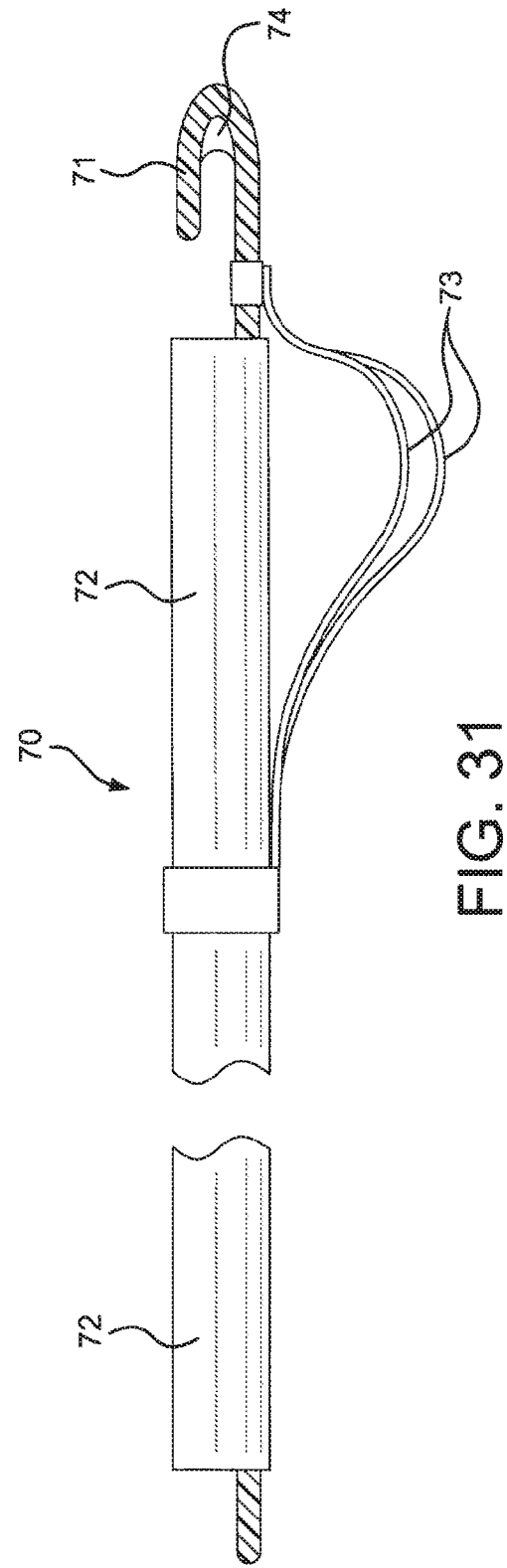
FIG. 31 illustrates an embodiment of the present invention.

In another embodiment, an electrically insulated cutting wire is contained within a delivery catheter or sheath (FIGS. 30-31). In preferred embodiments, the cutting wire is formed into a "U" or substantially hooked shape. Electrical insulation is removed from a portion of the cutting wire to expose an underlying electrically conductive wire. When energized with electricity, the exposed electrically conducting portion of the wire is used to cut tissue. Once the desired tissue is cut, the cutting wire is usually retracted within the catheter or sheath.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

EXAMPLES

Example 1

A catheter-based dissection septal cutting tool (1) of the present invention was constructed as follows (FIG. 12).

Figure 8:
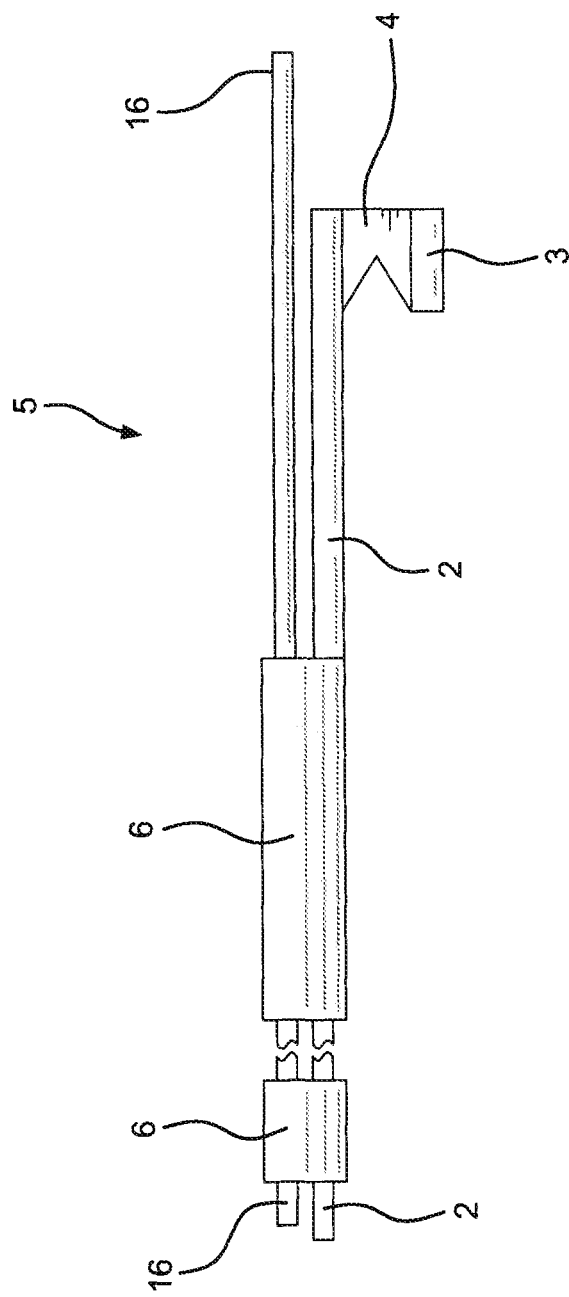
FIG. 8 illustrates a cutting blade assembly, an accompanying delivery catheter, and an optional guidewire.

Initially, a cutting blade assembly (5) having a movable, or translatable, V-shaped cutting blade (4) was constructed (FIG. 7) and subsequently attached to a delivery catheter (6) as illustrated in FIG. 8. The movable cutting blade (4) is controlled and actuated with movable elongate member (2).

A cutting blade (4) for the cutting blade assembly (5) was made from a sheet of 316L stainless steel (0.25 mm thick) (McMaster Carr, Elmhurst, Ill.). The stainless steel sheet was cut into a rectangular section measuring 0.63 cm long and 0.24 cm wide. A 0.10 cm long V-shaped notch was center cut along the length of the section. The apex of the V-shaped cut had an angle of thirty-five (35) degrees. The edges of the V-shaped notch were sharpened using a grinder to form cutting blade (4).

A movable elongate member (2) for the cutting blade assembly (5) was made from a length of stainless steel tubing. A ninety-two centimeter (92 cm) long tube made of 304 stainless steel (0.53 mm inner diameter and 1.04 mm outer diameter) was obtained (Ray's Dies and Tubing, Swanton, Vt.). A notch, one centimeter (1 cm) long and 0.254 mm wide, was cut in the stainless steel tube one centimeter (1 cm) from one end. The notch was subsequently used to receive and retain a non-cutting edge of cutting blade (4).

A cutting blade housing member (3) of the cutting blade assembly (5) was made from a length of stainless steel tubing. A one centimeter long (1 cm) tube made of 304 stainless steel (0.53 mm inner diameter and a 1.04 mm outer diameter) was obtained (Ray's Dies and Tubing, Swanton, Vt.). A 0.254 mm wide notch was cut in a side of the tube along the entire length of the stainless steel tube. The notch was subsequently used to receive and retain a non-cutting edge of cutting blade (4).

These three parts were combined as shown in FIG. 7. The blade (4) was inserted into the notches of the aforementioned stainless steel cutting blade-housing members (2, 3) and laser-welded in place such that the cutting edge faced the longer length of the 92 mm tube (3), thereby creating a cutting blade assembly (5).

The cutting blade assembly (5) was then attached on to a length of dual lumen polymeric tubing (FIG. 8). The polymeric tubing serves as a delivery catheter (6) and assists in delivery, positioning, and operation of the cutting blade assembly (5).

A delivery catheter (6) for the cutting blade assembly (5) was made from a sixty-five centimeter (65 cm) long (1.52 mm outer diameter) dual lumen (dual channel) 72 D polyether block amide (PEBA) tubing, commonly referred to under the trademark PEBAX®. The channels in the PEBA tubing were both 1.14 mm in diameter and located with their origins aligned to the centerline of the tubing such that the minimum wall thickness of tubing in any location was 0.254 mm from the outer surface of the tubing, on average. Starting at one end of the PEBA tubing, a four centimeter (4 cm) long, 0.38 mm wide, notch was cut lengthwise in tube material defining one channel, or lumen, of the tubing. The notched portion of the tubing (30) and the underlying channel was subsequently used to receive elongate member (2).

Flexible housing member (10) was constructed as follows. A 5.5 cm length of medium density polyethylene (PE) tubing (1.14 mm inner diameter, 1.65 mm outer diameter) was obtained and subsequently shape-formed on a 1.14 mm outer diameter PTFE-coated 304 stainless steel mandrel. The tubing was bent at each end. The bend was formed approximately 5 mm from each end of the PE tubing at a 140 degree angle. The length of the bent tubing was about 4 mm. The bent PE tubing was heat set by placing it in a forced air oven (Beaham Designs, Inc., Campbell, Calif.) set at 232 degrees centigrade (232° C.) for 30 seconds. A four centimeter (4 cm) long notch was cut along the length of the PE tubing starting at the end opposite from the bend. The notched tubing was subsequently used to receive and retain second cutting blade assembly member (3).

A displacement element assembly (20) having a plurality of displacement elements (7) was then constructed for subsequent attachment to the PEBAX® delivery catheter (6). In this embodiment, a seven centimeter (7 cm) long tube (3.3 mm inner diameter with a 0.25 mm wall thickness) made of nickel-titanium (NiTi) shape memory metallic alloy (Nitinol) was obtained (Memry Corp., Menlo Park, Calif.). The tube was then lasercut (Laserage Technology Corp., Waukegan, Ill.) to having six (6) strips with a rectangular cross-section (0.25 mm thick, 0.7 mm wide) and a notched collar at both ends of the displacement element (FIGS. 11A and 11B). All six strips were bent as shown in FIG. 3 and heat set in that shaping in forced air air oven (Beahm Designs, Inc., Campbell, Calif.) set at 450 degrees centigrade (450° C.) for fifteen minutes (15 min).

The notched collars (8, 9) of assembly (20) were placed over delivery catheter (6) with the displacement elements (7) oriented as shown in FIG. 12. The notches in the collars were located to permit cutting blade assembly (5) to move freely in the notch of delivery catheter (6). The end of the notched collar (9) located farthest from the end of delivery catheter (6) was then bonded to the delivery catheter (6) using a cyanoacrylate adhesive. The end of the notched collar (8) located nearest the end of delivery catheter (6) was not attached to delivery catheter (6) and allowed to freely move along the length of delivery catheter (6).

The cutting blade assembly (5) was attached to delivery catheter (6) by fully inserting the free end of movable elongate member (2) into the notched channel of the dual lumen delivery catheter (6). The unused channel, or luminal space, of the delivery catheter (6) is available for containing a guidewire (16) or other device (FIG. 9).

The flexible housing member (10) was attached to cutting blade housing member (3) by placing the aforementioned notched end of flexible housing member (10) over the second cutting blade housing member (3) (FIG. 9). Flexible housing member (10) was oriented so the bent tip extended toward, and preferably touched delivery catheter (6). The notched end of the flexible housing member (10) was then affixed to delivery catheter (6) by opening the lumen to lay flat on delivery catheter (6) and placing a 5 mm length of fluorinated ethylene propylene (FEP) heat shrink tubing (3.8 mm inner diameter, 4.2 mm outer diameter) over the open end of the flexible housing member (10) and the delivery catheter (6) (FIG. 9). Support mandrels (1.14 mm outer diameter) were placed inside both channels of the dual lumen delivery catheter (6) to maintain the dimensions of the tubing during a subsequent heat shrinking process. Heat was applied to the fluorinated ethylene propylene (FEP) heat shrink tubing until the tubing shrunk over the flexible housing member (10) and adjacent delivery catheter (6) by placing the construction in a forced air oven set at 233 degrees centigrade (232° C.) for thirty seconds (30 sec).

Referring to FIG. 10, one end of a length of hollow housing wire (13), 0.66 mm inner diameter, 1 mm outer diameter, was attached with cyanoacrylate glue (Loctite 4011, Loctite Corporation, Rocky Hill, Conn.) to the delivery catheter (6) in the same lumen as the first cutting blade housing member (2). Using a one millimeter (1 mm) diameter biopsy punch, a hole was cut onto the top surface of the flexible housing member (10) and the other end of hollow housing wire was inserted into the aforementioned hole and attached to the flexible housing member (10) with cyanoacrylate glue (Loctite 4011, Loctite Corporation, Rocky Hill, Conn.) as shown in FIG. 10.

As illustrated in FIGS. 10 and 12, a Nitinol wire (15), approximately 120 cm in length and 0.3 mm in diameter was inserted into the free end of delivery catheter (6), through first cutting blade housing member (2), hollow housing wire (13), second cutting blade housing member (3), and flexible housing (10), leaving both ends of the Nitinol (15) wire exposed.

Figure 32:
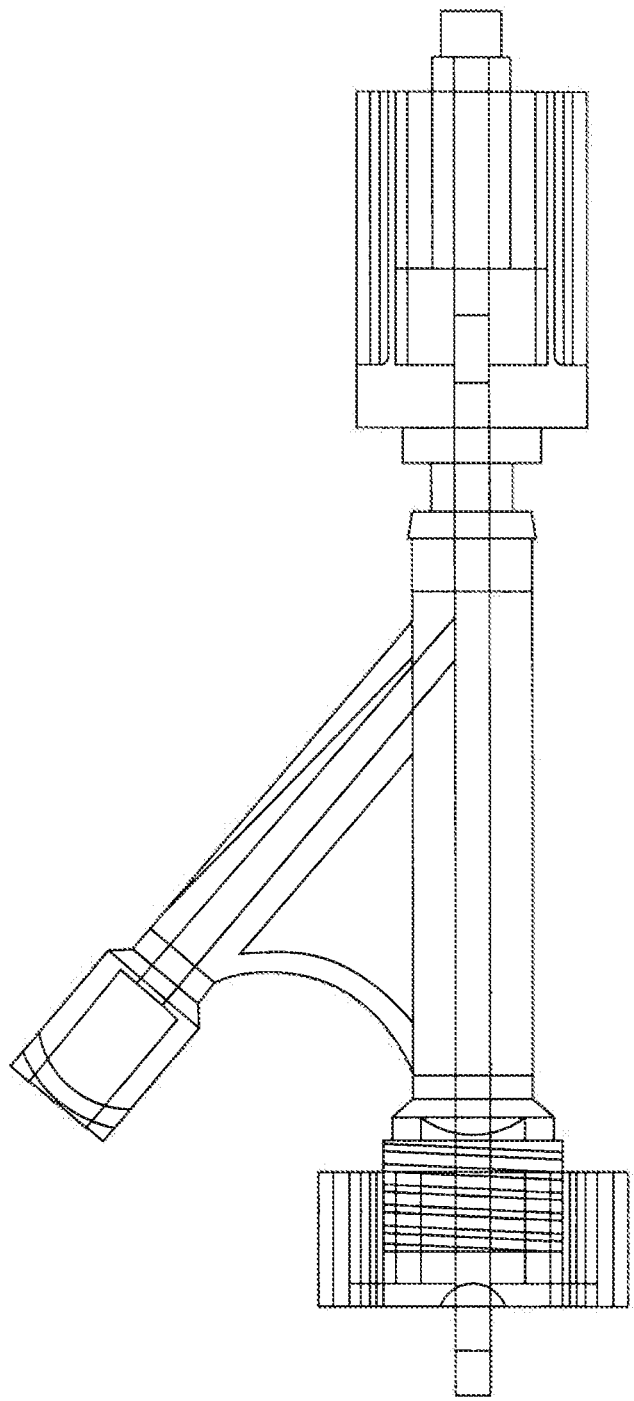
FIG. 32 illustrates a catheter hub assembly.

A hub assembly (Part #80394, Qosina, Edgewood, N.Y.) was obtained and attached to the free end of delivery catheter (5) with cyanoacrylate glue (Loctite 4011, Loctite Corporation, Rocky Hill, Conn.) (FIG. 32). An approximately 1.2 mm hole, located about 10 cm from the end of the delivery catheter (5) was cut into the side of the delivery catheter (6) to provide access to the heretofore unused channel of the PEBAX® tubing. A 0.98 mm guidewire (Amplatz, AGA Medical Corp. Plymouth, Minn.) was obtained and inserted through the hole of the delivery catheter (5) and advanced until exiting the opposite end of the delivery catheter (6).

In use, the completed septal cutting tool device can be placed entirely within the true lumen or advanced through the false lumen. Cutting can be achieved by either pulling the blade distally with respect to the delivery catheter and/or pulling the entire device distally.

Example 2

Figure 14:
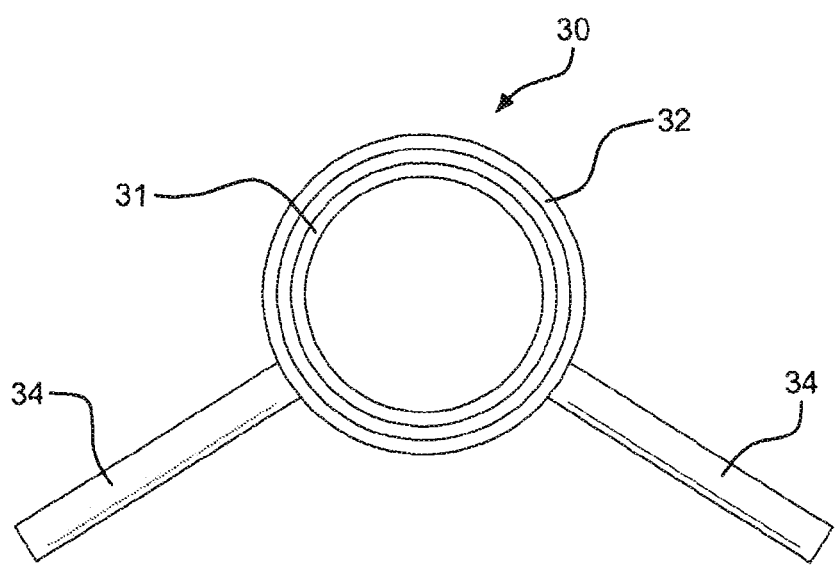
FIG. 14 illustrates a cross-sectional view of a delivery catheter with displacement elements.

A cutting tool having a movable cutting blade and actuated, flexible, displacement elements was constructed as follows (FIGS. 14 and 15).

A delivery catheter (30) having one tubular component (31) placed inside another tubular component (32) in a coaxial relationship was obtained from W.L.Gore & Associates, Inc., Flagstaff, Ariz. The catheter is currently used in conjunction with the GORE VIABIL® Biliary Endoprosthesis.

The delivery catheter had a 3.07 mm outer diameter and is compatible with delivery systems and devices having diameters in the range of ten French (10 Fr). The delivery catheter has a component for mounting the GORE VIABIL® Biliary Endoprosthesis extending from one end of the catheter. The mounting component is a solid metallic shaft with a bulbous feature on the end of the shaft to assist in retaining the endoprosthesis on the shaft. The metallic shaft and bulbous feature were removed from the delivery catheter by cutting. The delivery catheter had a blunt end with both tubular components of the delivery catheter flush with one another.

A circumferential cut was made in the outer tubular component of the delivery catheter approximately three centimeters from the blunt end. The severed portion of the outer tubular component was removed from the delivery catheter leaving the inner tubular component extending three centimeters beyond the outer tubular component. The removed three centimeter portion of the outer tubular component was cut into two tubular pieces, each 1.5 cm in length.

The inner tubular component (31) extending beyond the outer tubular component (32) of the delivery catheter (30) was cut into a shape delimiting two holes capable of mating with each of the two 1.5 cm tubular pieces. One end of each 1.5 cm tubular pieces was cut in a shape that permitted the two tubular pieces to be mated and attached to the inner tubular component in a Y-shaped configuration (FIG. 15). A cutting blade (33) was subsequently placed in the Y-shaped construction to form a cutting blade assembly.

To attach the two 1.5 cm tubular pieces to the inner tubular component of the delivery catheter, two polytetrafluoroethylene (PTFE) coated mandrels (approximately 10 cm long and 1.5 mm in diameter) were obtained (New England Precision Grinding Inc., Holliston, Mass.). Approximately 5 cm of one PTFE-coated mandrel was inserted into one of the holes formed in the inner tubular component. Approximately 5 cm of another PTFE-coated mandrel was inserted into the remaining hole formed in the inner tubular component.

One of the 1.5 cm tubular pieces was placed over an exposed end of one of the PTFE-coated mandrels. The other 1.5 cm tubular piece was placed over an exposed end of the second PTFE-coated mandrel. The tubular pieces were pressed against the cut end of the inner tubular component in a Y-shaped configuration. A length of heat-shrink tubing (ZEUS Inc., Orangeburg, S.C.) having a 4.6 mm outer diameter was placed over the inner tubular component and the two 1.5 cm tubular pieces.

The construction was placed inside the nozzle of a hot air system (Beahm Designs Inc., Campbell, Calif.) set at 218 degrees C. until the heat-shrink tube contracted around the inner tubular component and the two 1.5 cm tubular pieces fixing the three parts in place. Additional heat was applied and caused the three parts to melt together to form a Y-shaped assembly. A cutting blade was subsequently attached to the Y-shaped assembly. Once cooled, the PTFE-coated mandrels were removed from the assembly. The heat shrink tubing was removed from the assembly by cutting with a razor blade.

A cutting blade (33) for the assembly was formed from a number eleven (11) razor blade (American Safety Razor Co., Stanton, Va.). To form the cutting blade, approximately 9 mm of the tip of the razor blade was removed from the razor blade. A non-cutting edge of the razor blade tip was placed in the crux of the Y-shaped portion of the assembly, such that the blunt end was adjacent to the junction of the three tubes and the cutting edge was exposed. The blade was fixed in place with cyanoacrylate glue and allowed to dry. The cutting blade assembly thus formed was trimmed to have an overall length of about three centimeters.

Opposite ends of displacement elements (34) were attached to the outer tubular component (32) of the delivery catheter (30) and to the inner tubular component (31) at the location of the cutting blade assembly as illustrated in FIG. 14 (not to scale). In this embodiment, a sixty-five centimeter (65 cm) length of the outer tubular component (32) of the delivery catheter (30) was used. In this embodiment, the displacement elements (34) were made of a nickel-titanium metal alloy (Nitinol) wire. A PTFE-coated mandrel (100 cm long, 2.75 mm diameter) was obtained (New England Pecision Grinding, Inc., Holliston, Mass.) for subsequent use in a heat shrinking step. Displacement elements were made from two 7.5 cm lengths of Nitinol wire (0.38 mm diameter) (New England Pecision Grinding, Inc., Holliston, Mass.). A 1 cm length of nylon tubing (36) (4.3 mm outer diameter and 0.13 mm wall thickness) was obtained and used to affix the displacement elements (34) to the outer tubular component (32) of the delivery catheter (30).

The nylon tubing (36) was placed over the outer tubular component of the delivery catheter so the nylon tubing was flush with the end of the outer tubular component. A first Nitinol wire displacement element (34) was placed between the inner surface of the nylon tube (36) and the outer surface of the outer tubular component (32) so the wire was seven millimeters (7 mm) inside the nylon tube (36) and was oriented substantially parallel to the longitudinal axis of the outer tubular component (32). The second Nitinol wire displacement element (34) was similarly placed and positioned under the nylon tubing (36) on the outer tubular component (32). The second Nitinol wire displacement element (34) was positioned one hundred twenty degrees from the first Nitinol wire when viewed in cross-section (FIG. 14). FIG. 15 illustrates the positioning of the displacement elements (34) relative to the cutting blade (33). In FIG. 15, one displacement element (34) projects out of the plane of the page and one displacement element (34) projects into the plane of the page (not shown).

The PTFE-coated mandrel was inserted into the lumen of the outer tubular component of the delivery catheter. A five centimeter (5 cm) length of polyethylene terephthalate (PET) heat shrink tubing (not shown) (4.3 mm inner diameter and 0.05 mm wall thickness) was obtained (Advanced Polymers, Inc., Salem, N.H.) and centered over the nylon tubing (36) and heated until the nylon tubing (36) melted and anchored the ends of the first and second Nitinol wire displacement elements (34) to the outer tubular component (32) of the delivery catheter (30). The PTFE-coated mandrel was removed and the PET shrink tube was longitudinally cut and removed.

The cutting blade assembly was then attached to the inner tubular component (31). Prior to attaching the cutting blade assembly to the inner tubular component, the inner tubular component of the delivery catheter was threaded through the outer tubular component until the inner tubular component extended a few centimeters beyond the end of the outer tubular component. The inner tubular component was seventy-five centimeters (75 cm) in length.

A PTFE-coated mandrel (approximately 100 cm long and 0.94 mm diameter) was placed inside the inner tubular component (31) until the mandrel extended a few centimeters beyond the end of the inner tubular component.

Prior to attachment of the cutting blade assembly to the inner tubular component (31), a 5 cm length of PET heat shrink tubing (4.3 mm inner diameter, 0.05 mm wall thickness) was obtained (Advanced Polymers, Inc., Salem, N.H.) and loosely placed over the outer tubular component (32) for subsequent use in attaching the displacement elements (34) to the outer tubular component (32).

In addition, a three centimeter (3 cm) length of PET heat shrink tubing was advanced the length of the tubular portion of the outer tubular component until it resided underneath each of the two displacement elements and over the inner tubular component of the delivery catheter.

To attach the cutting blade assembly to the inner tubular component (31) of the delivery catheter (30), two PTFE-coated mandrels (approximately 10 cm long and 0.46 mm diameter) were obtained (New England Pecision Grinding, Inc., Holliston, Mass.). One mandrel was placed into each lumen of the bifurcated portion of the Y-shaped cutting blade assembly. Approximately half the length of a 0.5 cm piece of nylon tubing (4.3 mm outer diameter and 0.13 mm wall thickness) was placed over the "bottom" linear section of the Y-shaped cutting blade assembly. The remaining half of the 0.5 cm piece of nylon tubing (non-shown) extended beyond the end of the cutting blade assembly.

The "bottom" linear section of the Y-shaped cutting blade assembly and outer nylon tubing was placed over the free end of the approximately 100 cm PTFE-coated mandrel projecting from the end of the inner tubular component. The cutting blade assembly was brought into contact with the free end of the inner tubular component. The 0.5 cm length of nylon tubing (non-shown) covered both the cutting blade assembly and the inner tubular component. The 3 cm piece of PET heat shrink tubing was advanced to cover the cutting blade assembly and the inner tubular component. Sufficient heat was applied to the construction to cause the heat shrink tubing to contract around the nylon tubing and for the nylon tubing to melt and bond the cutting blade assembly and inner tubular component together. The PET heat shrink tubing was then cut away from the construction.

The unattached ends of the Nitinol wire displacement elements (34) were then attached to the inner tubular component (31) and cutting blade assembly. A second piece of nylon tubing (37) was positioned near the bifurcation of the Y-shaped cutting blade assembly. The unattached end of each Nitinol wire was placed near the bifurcation of the Y-shaped cutting blade assembly under a second piece of nylon tubing (37). The five centimeter (5 cm) piece of PET heat shrink tubing was advanced until the tubing covered the free ends of the Nitinol wire displacement elements (34) and the underlying nylon tubing. Sufficient heat was applied to the construction to cause the heat shrink tubing to contract around the nylon tubing and for the nylon tubing to melt and bond the Nitinol wire displacement elements (34) and the cutting blade assembly together (FIG. 15). The PET heat shrink tubing was then cut away from the construction.

In clinical practice, two guidewires (35) would be utilized, one being advanced through one lumen of the "Y" shaped distal end and the other wire through the remaining lumen. One guidewire would be advanced into the true vessel lumen and the other into the false lumen. The catheter would track along both wires up to the dissected septum. Prior to cutting the septum, the outer member of the catheter would be advanced forward while not advancing the inner member, thereby causing curving of the displacement elements. As the displacement elements bow, the elements press against the blood vessel wall and position the cutting blade assembly in contact with septal tissue as the tissue is cut. In some embodiments, the cutting tool is configured to collapse over or around the cutting blade to confine and shield the cutting blade during delivery and removal of the invention.

Example 3

This example describes the construction of an embodiment of the present invention (40) having a cutting blade assembly (42) attached to a catheter (44) (FIG. 16). The cutting blade assembly (42) has a pair of remotely actuated scissor-like cutting blades (41). The invention also has a plurality of flexible displacement elements (43) attached to the cutting blade assembly (42) and the catheter (44).

Figure 17:
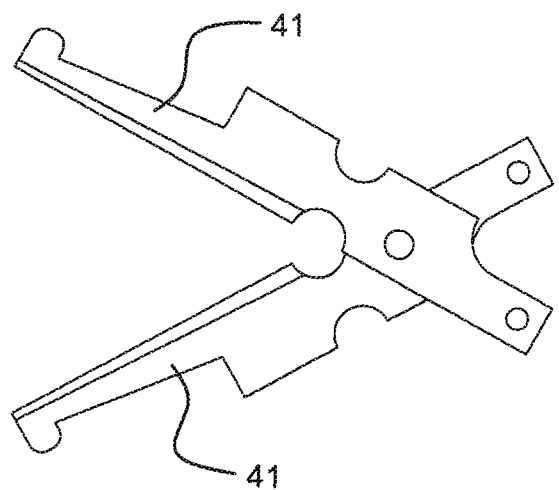
FIG. 17 illustrates a cutting blade of the present invention.

Cutting blades (41) for the cutting blade assembly (42) were constructed as follows. A small bore stainless steel tube was obtained (1.6 cm long, 2.8 mm outer diameter, 2.4 mm inner diameter, Microgroup, Inc., Medway, Mass.). Approximately 1.5 mm from one end of the tube a 0.8 mm diameter hole was drilled through both walls of the tube. A 5.5 mm long, 1.5 mm wide slot was ground into the same end as the holes, perpendicular to the axis of the holes. A second slot of the same dimensions was ground into the opposite side of the tube. Two cutting blades were made from tool steel. The blades were placed inside the tube, aligned with the holes, and secured in place with 0.79 mm diameter pin. The pins were cut flush with the sides of the tube and gently hammered in order to mushroom the ends (FIG. 17).

Figure 18:
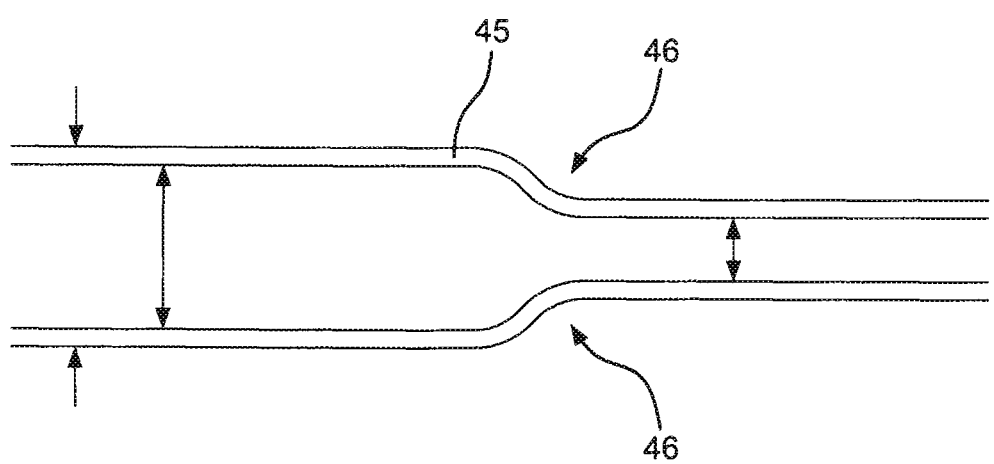
FIG. 18 illustrates a delivery catheter.

A catheter assembly (44) was made in the following manner. A polymer block amide having a blue color sold under the tradename PEBAX® tube (45) was obtained (60 cm long, 3.3 mm outer diameter, 2.7 mm inner diameter). One open end of the tube was gradually enlarged by introducing increasingly larger diameter PTFE-coated mandrels into the open end with the application of heat. The mandrels were 2.77 mm, 2.79 mm, and 2.82 mm diameter, respectively. Each mandrel was advanced 3.5 cm into the open end of the blue PEBAX tube. Heated air (approx. 224° C.) was applied to the PEBAX tube in the area of the underlying mandrel. The outer diameter of the finished PEBAX tube was 3.3 mm (FIG. 18).

Figure 19:
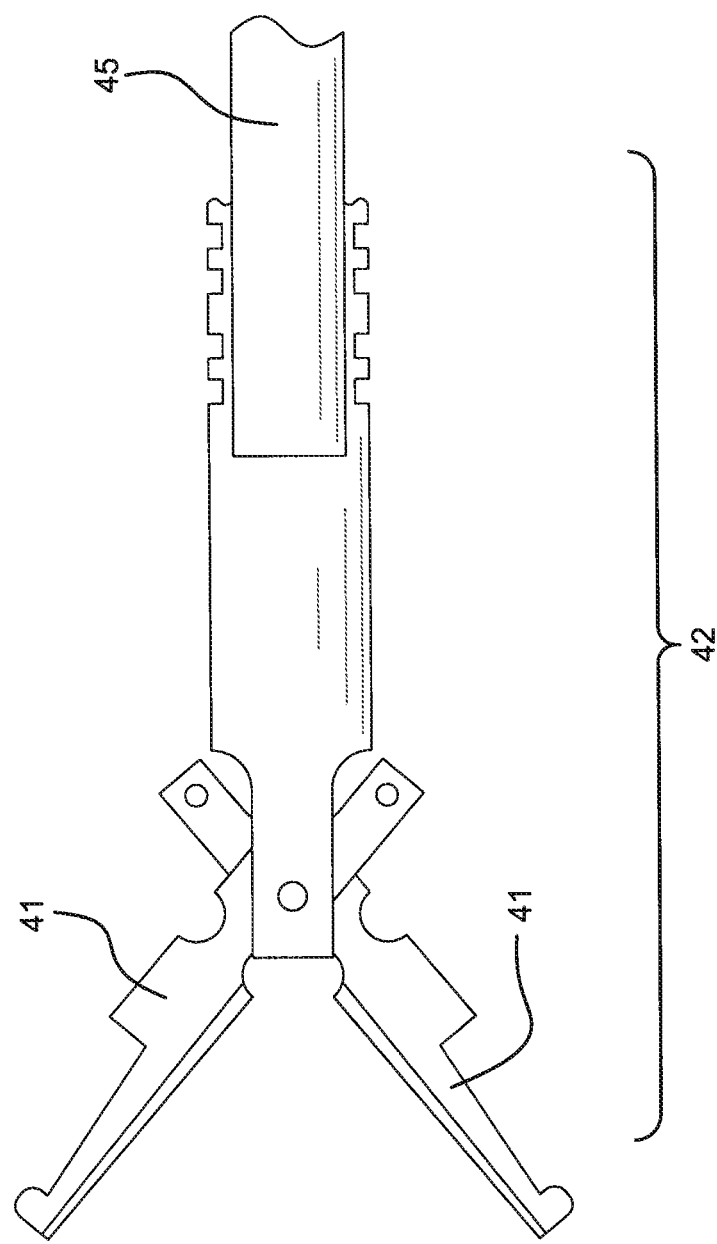
FIG. 19 illustrates an embodiment of the present invention.

Two holes (46) were drilled approximately 3.5 cm from the enlarged end of the PEBAX tube. The holes were 180 degrees apart and 0.64 mm in diameter (FIG. 18). A catheter hub (47) was obtained (part nos. 88416 and 80343, Qosina, Edgewood, N.Y.). The smaller end of the blue PEBAX tube (45) was inserted inside part number 88416 and secured with UV activated glue. Part number 80343 was attached to the luer fitting of the "Y" portion of part number 88416. A 75 cm long, 2.01 mm outer diameter, 1.46 mm inner diameter length of a PEBAX® tubing was obtained with attached hub. This tubing was obtained and introduced into part no. 80343 until it exited the end of the blue PEBAX tube (45). The aforementioned cutting blades (41) were crimped to the end of this tubing to form a cutting blade assembly (42) (FIG. 19).

Figure 20:
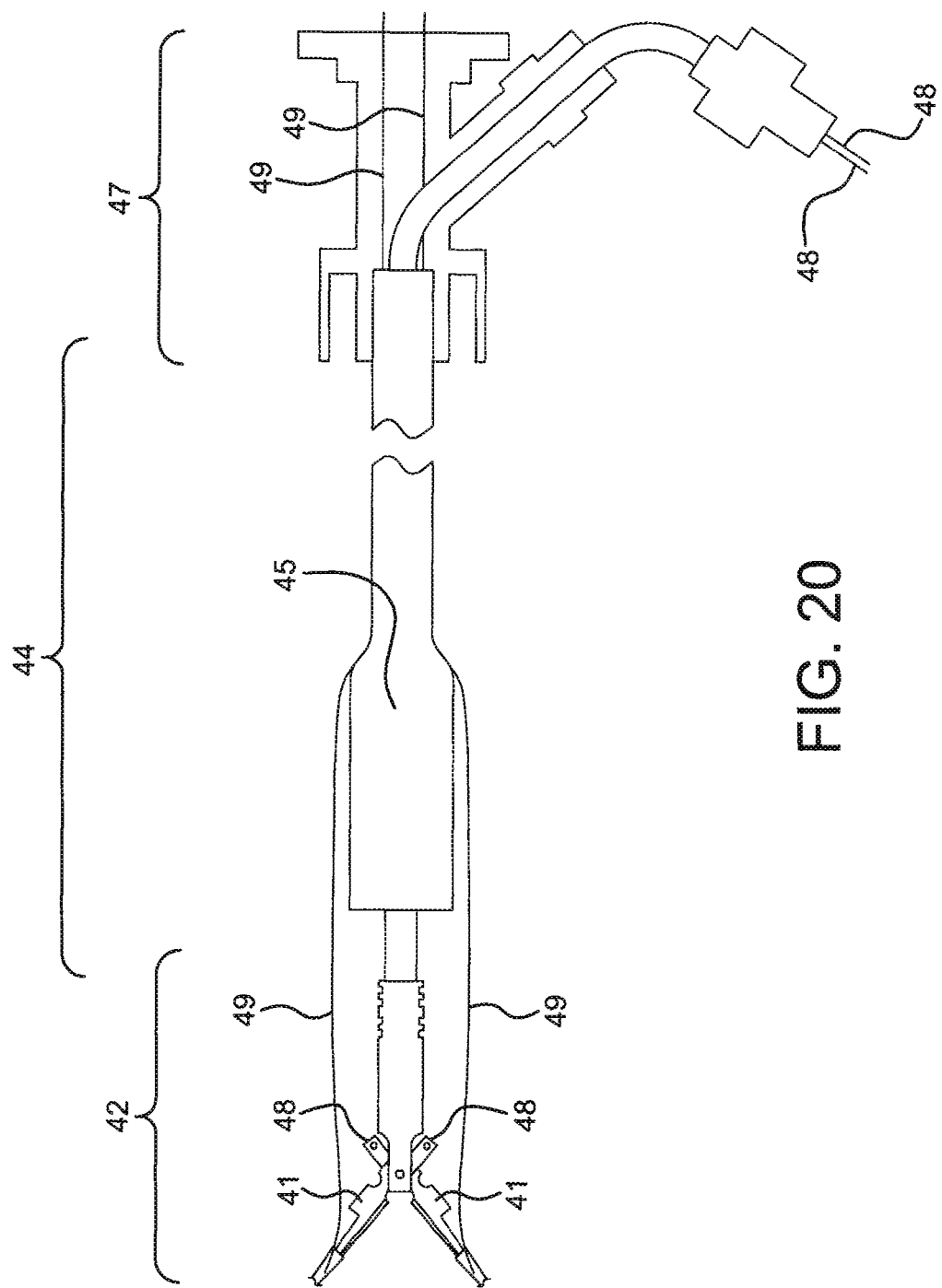
FIG. 20 illustrates an embodiment of the present invention.

Two stainless steel actuating wires (48) (90 cm long, 0.44 mm diameter) for the cutters (41) were inserted into the end of the catheter opposite the cutting blade assembly and advanced through the catheter to the cutting blades where they were attached to the holes in the blades (FIG. 20). Each wire was inserted into the hole of one blade and bent 180 degrees and trimmed. Two atraumatic tips (49) were made of a heat-shrinkable polymeric material. Each tip was placed over an end of a cutting blade (41) and heat applied to reshape and attach the atraumatic tip the cutting blade end. The cutting blades (41) were sharpened with honing tool.

Flexible displacement elements (43) were attached to the cutting blade assembly and catheter as follows. White PEBAX® tubing (46) (50 cm long, 4.8 mm outer diameter, and 0.38 mm wall thickness) was obtained and placed coaxially on top of the catheter (45) and the cutter assembly (42) so 5.5 cm of the blue PEBAX® tubing (45) was exposed. A two centimeter (2 cm) long, 6.35 mm inner diameter heat shrink tubing was obtained and placed over the white PEBAX® tubing. Two 7.5 cm lengths of 0.38 mm diameter Nitinol wire were obtained (New England Pecision Grinding, Inc., Holliston, Mass.). The Nitinol wires were then placed between the inner surface of the heat shrink tubing and the outer surface of the white PEBAX tubing (46), such that the wire was two centimeters (2 cm) inside the heat shrink tubing. The two wires were located 120 degrees apart along the circumference of the tubing. The heat shrink tubing was heated to secure the wires. A 0.5 cm long, 6.35 mm inner diameter heat shrink tubing was obtained and placed over the blue PEBAX® tubing (46). The wires were secured in the same manner as described above. An ethyl cyanoacylate adhesive (Loctite 401, Loctite Corporation, Rocky Hill, Conn.) was applied to the junctions of the heat shrink tubing, displacement elements (43), blue PEBAX® tubing (45), and white PEBAX® tubing (46).

As illustrated in FIG. 16, one displacement element (43) was positioned to one side of the cutting blades (41) and the other displacement element (43) is positioned to the other side of the cutting blades (41).

Figure 21:
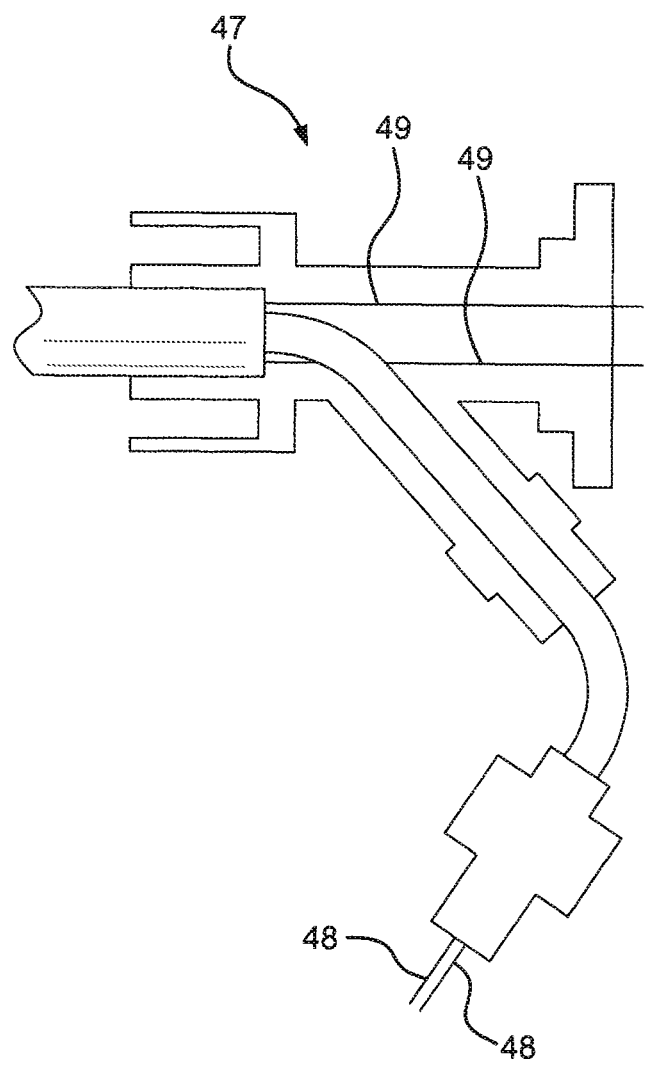
FIG. 21 illustrates a hub embodiment of the present invention.

Two 0.36 mm guidewires (49) were obtained (Cordus, Stabilizer). One guidewire (49) was inserted into one hole of the blue PEBAX® tube (45). The other guidewire (49) was inserted through the other hole in the blue PEBAX® tube (45). Both wires were advanced and exited a hemostatis valve the end of the catheter assembly (FIGS. 20 and 21).

In practice, one guidewire would be advanced into the true vessel lumen and the other into the false lumen. The catheter would track along both wires up to the dissected septum. Advancing the white PEBAX® tube would move the flexible displacement elements and position the cutting blade assembly at a desired location. The cutting blade assembly would be advanced to expose the cutting blades. The actuating wires would be operated to open the blades for cutting. The entire catheter would be advanced in order to cut dissection tissue. The white PEBAX catheter and flexible displacement elements would cooperate to position and stabilize the cutting blades as the invention is advanced through the vasculature and used to cut the septum of dissected tissue.

Example 4

Figure 22:
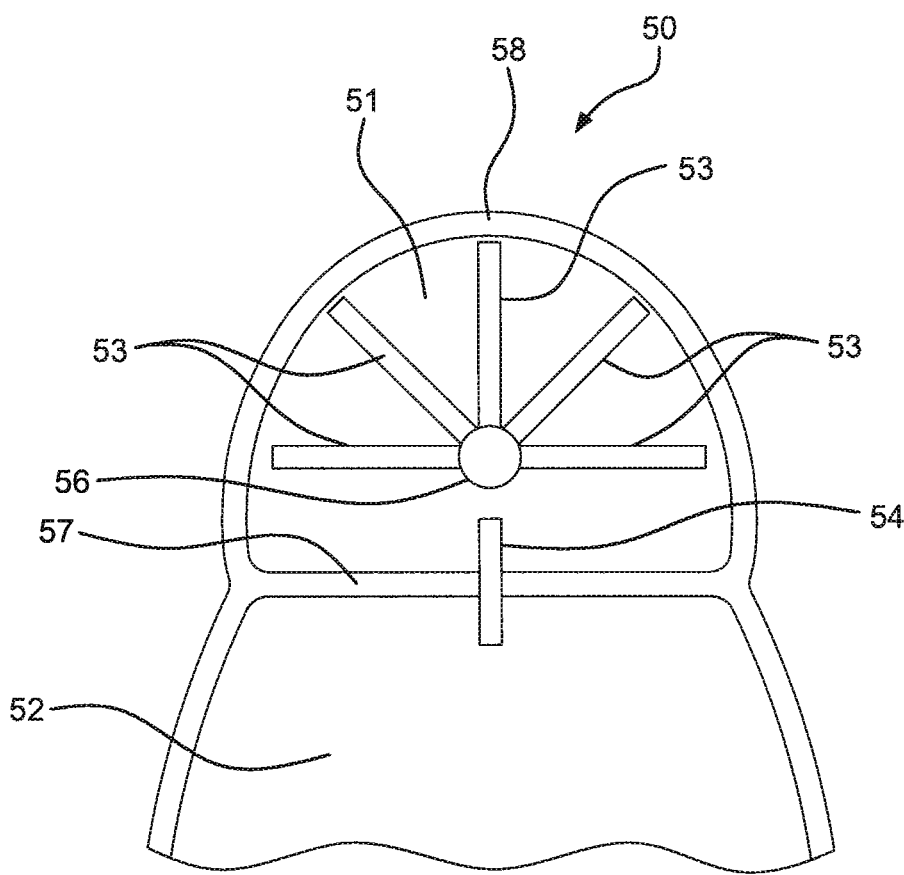
FIG. 22 illustrates an embodiment of the present invention.
Figure 23:
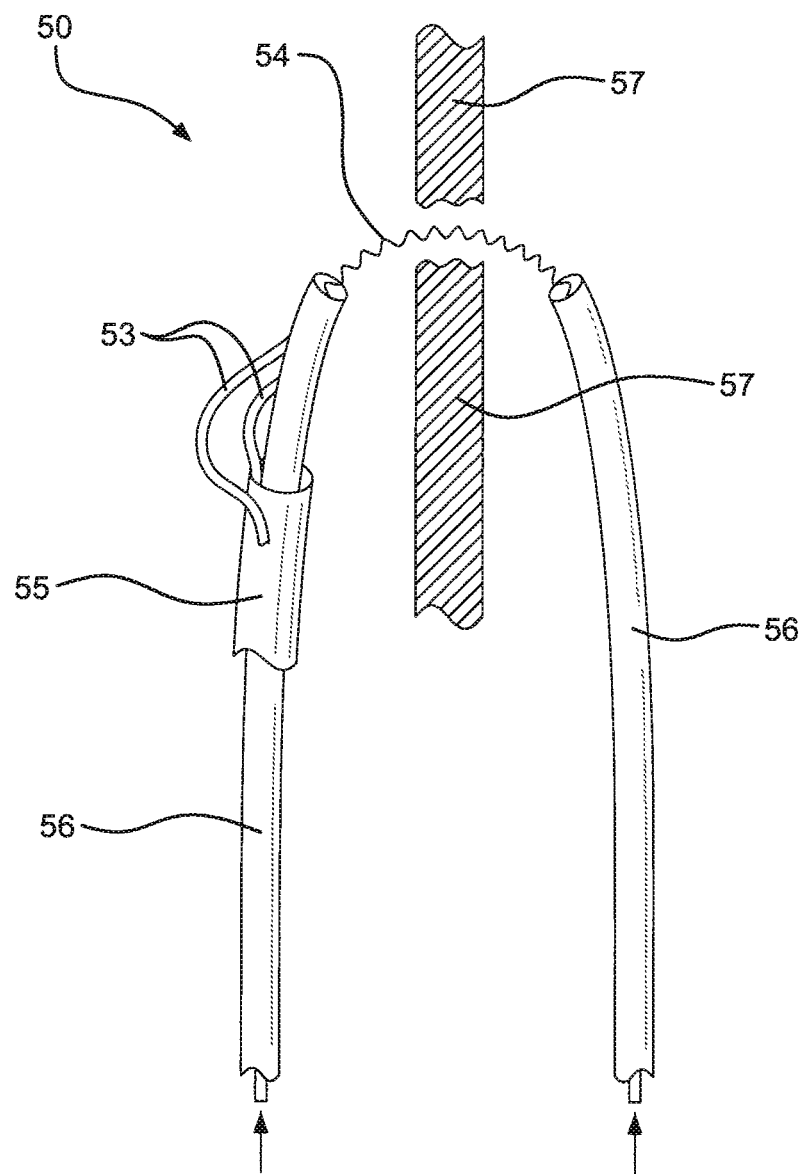
FIG. 23 illustrates an embodiment of the present invention.

This example describes an embodiment of the present invention (50) having wire (54) with a serrated cutting edge to cut septal tissue (57) of a dissection. In use, the serrated cutting wire is delivered to a treatment site within a delivery catheter (55). The delivery catheter is designed to permit the cutting edge of the serrated wire to be exposed to cut septal tissue. The device of this embodiment also has flexible displacement elements (53) or other flexible elongate members configured to assist in positioning the cutting wire at a desired anatomical location and in maintaining the cutting wire in contact with tissue as the tissue is being cut (FIGS. 22 and 23).

A delivery catheter for the cutting wire was made as follows. Two lengths of PEBAX® dual lumen tubing (approximately 95 cm in length, a 2.3 mm outer diameter, and a hardness shore 63D) were obtained (Extrusioneering Inc, Temecula Calif.). One lumen in each length of dual lumen tubing had a 0.97 mm inner diameter. The other lumen in each length of dual lumen tubing had a 0.6 mm inner diameter.

A piece of polyolefin heat shrink tubing, approximately 1 cm long, 3.0 mm diameter, and 0.2 mm wall thickness (Part #207, Insulation Plastics, Inc., Hermitage, Tenn.) was placed over one end of each length of dual lumen delivery catheter tubing. Approximately half of the heat shrink tubing covered the underlying delivery catheter and the remaining half of the heat shrink tubing extended beyond the end of the delivery catheter. Heat was applied to the heat shrink tubing with the use of a hot box (Balloon Development System Model 210-A, Beahm Designs, Campbell, Calif.). The heat shrunk pieces served as pliable, cut-resistant, tips on the end of the each length of dual lumen tubing. The pliable, cut-resistant, tips had open ends and were in fluid communication with each luminal space of each length of dual lumen delivery catheter tubing.

A Y-shaped catheter hub (not shown) was obtained (part #80376 hemostasis Y valve, Qosina, Edgewood, N.Y.) and attached to the end of each dual lumen delivery catheter tubing opposite the heat shrunk tubing. The Y-shaped catheter hub included a port for passing fluids (i.e., flushing) through the hub and attached catheter tubing. A 0.1 ml syringe was obtained (part # C3302 BD luer slip syringe, Qosina, Edgewood, N.Y.) and the end of the syringe glued into the flushing port of the hub using a UV curable glue (DYMAX UV curable adhesive #204-CTH, Torrington, Conn.). The plunger shaft of the syringe was removed and replaced with a 4.3 mm diameter, 0.8 mm wall thickness, 8 cm long PEBAX tube (hardness shore 70D, Extrusioneering Inc, Temecula Calif.). A male luer fitting was attached to one end of the tube.

The rubber plunger seal was removed from the syringe plunger. A hole, approximately 0.75 mm in diameter, was drilled in the center of the seal. The seal was glued to the end of the PEBAX tube without the luer fitting using a UV curable glue. A length of PEBAX tubing (approximately 1 mm outer diameter and 0.06 mm wall thickness) was inserted through the seal and through the entire length of the replacement plunger shaft. This tube was added to serve as a support sheath for a wire to be added later.

A mechanical device (not shown) for moving the serrated cutting edge back and forth was initially attached to the delivery catheter as follows. A battery operated toothbrush was obtained (children's battery-powered toothbrush, Colgate-Palmolive Company, New York, N.Y.) and fitted inside a cylindrical housing that contained a female luer fitting at one end and a hole that enabled access to the on-off switch of the toothbrush. The end of one length of PEBAX dual lumen tube without the heat shrink tubing was secured to the flushing port of the hub with UV curable glue and heat shrink tubing.

Flexible displacement elements (53) were attached to the delivery catheter portion of the present invention as follows. A polymeric tube (55) was obtained (Extrusioneering Inc, Temecula Calif.). The polymeric tube was a PEBAX® dual lumen delivery catheter, hardness shore 63D, 85 cm in length having a 3.5 mm outer diameter, and a 2.5 mm inner diameter. The polymeric tube was placed coaxially over the PEBAX tube (56) (2.3 mm outer diameter) that was attached to the catheter Y-shaped hub. Flexible displacement elements (53)

in the form of two 7.5 cm length sections of 0.38 mm diameter Nitinol wire (Fort Wayne Metals, Ft. Wayne, Ind.) were attached approximately 5 mm from the proximal end of the outer tube (55) and approximately 5 mm from the end of the 2.3 mm diameter PEBAX tube (56). The flexible displacement elements (53) were spaced approximately 120 degrees apart. The flexible displacement elements were attached to the outer 3.5 mm diameter tube and the inner 2.3 mm diameter PEBAX tube by a potting method utilizing FEP shrink tubing (Zeus, Inc., Orangeburg, S.C.) and the application of localized heat. Upon advancing the outer tube toward the distal end of the PEBAX tube, the flexible displacement elements assumed a curved configuration, causing them to bow radially outward.

The serrated cutting wire (54) was attached to the mechanical device (not shown) as follows. A 220 cm length of 0.1 mm steel wire was obtained (MP-35N Medical Wire, Lot #10467, Xylem Company, Wayzata, Minn.). The wire was secured with UV curable glue to the vibrating element of the toothbrush. The wire was then inserted through, in order, the female luer fitting at the end of the housing, the male luer fitting at the end of the replacement plunger, the 1 mm tube attached through the seal, the flushing hub, the smaller hole of the dual lumen PEBAX tube, and entirely through the cut-resistant tip of PEBAX tube. The wire was then inserted through the cut-resistant tip of the other length of PEBAX tubing and entirely through that length of PEBAX tubing. With the replacement plunger retracted to half of the syringe stroke (i.e., to the 0.5 ml mark), the free end of the wire was slightly tensioned in order to achieve contact between the ends of the cut-resistant tips.

Two knots were tied in the free end of the steel wire where it exited the PEBAX tube. A 0.96 mm diameter PTFE coated mandrel was inserted into the larger hole of the PEBAX tubing. FEP heat shrink tubing with the dimensions 3.175 mm inner diameter, 0.25 mm wall thickness (Zeus Industrial Products, Orangeburg, S.C.) was placed over the distal two centimeters (2 cm) of the PEBAX tube and the end of the tube was placed in a hot box set to 215 degrees centigrade (215° C.) until the knot was secured in the smaller lumen. After cooling under ambient conditions, the PTFE coated mandrel was removed and the heat shrink tubing was removed with by cutting it with a razor blade.

When the replacement plunger was moved, the gap between the cut-resistant tips increased in length, exposing the wire, enabling it to be used as a septum cutting tool. When the mechanical device was turned on, the serrated cutting wire moved back and forth at the cutting site and aided in cutting septal tissue. The device is illustrated in FIGS. 22 and 23.

In clinical use, the delivery catheter is advanced through the vasculature to the site of a dissection having a true lumen (51) and a false lumen (52).

The free end of the cutting device (50) is advanced through one lumen of a dual lumen introducer sheath until reaching the proximal end of the dissection septum (57). Advancing the outer tube will cause the bowed wires to both contact the vessel wall (58), displace, center, and stabilize the position of the cutting blade within the true lumen (51). Another device capable of capturing the free end of cutting device is introduced through the second lumen of the introducer sheath, used to snare the end of the cutting device and deliver it through the second lumen and outside the body. The wire is then pulled down into the septum allowing the wire to serve as a cutting element.

Example 5

This example describes an embodiment of the present invention (60) having flexible displacement elements (63) attached to a delivery device, such as a catheter (65, 66). The flexible displacement elements (63) are suitable for use on a variety of embodiments of the present invention (FIGS. 24 and 25).

In this example, an inner polymeric tube (66) was placed in coaxial relationship within an outer polymeric tube (65). The inner tube (66) readily moved within the outer tube (65). One end of the inner tube extended beyond the outer tubing a length sufficient to attach two flexible strips to both the inner and outer tubing. The flexible strips serve as displacement elements.

An inner tube (66) made of PEBAX® was obtained (Specialized Engineering LLC, Stockton, Calif.). The inner tube had a 3 mm OD×2 mm 72 d. An outer tube (65) made of PEBAX tube was obtained (Specialized Engineering LLC, Stockton, Calif.). The outer tube had a 4 mm OD×3.1 mm ID 72 d. The inner tube was placed inside the outer tube in a coaxial relationship.

Figure 24:
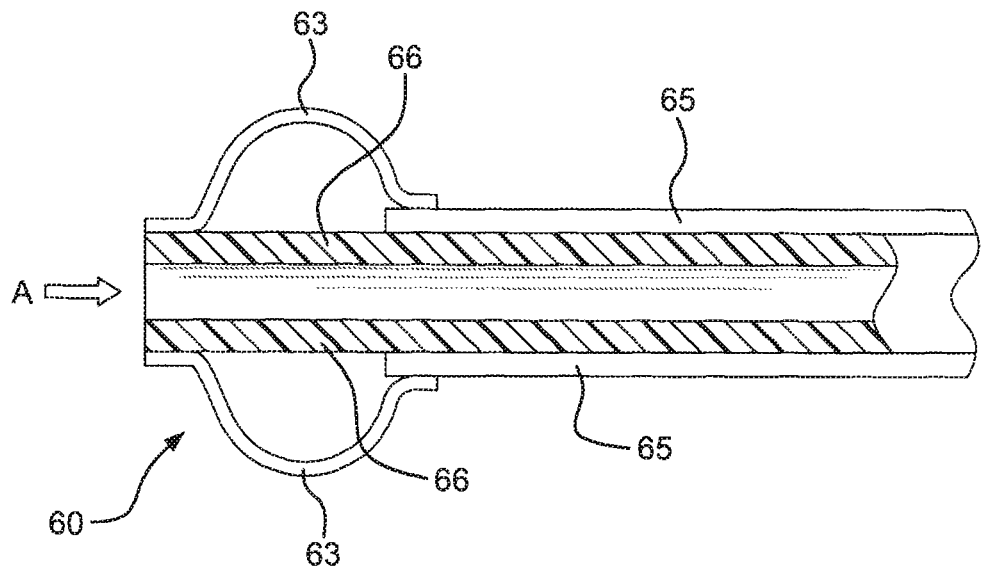
FIG. 24 illustrates an embodiment of the present invention.
Figure 25:
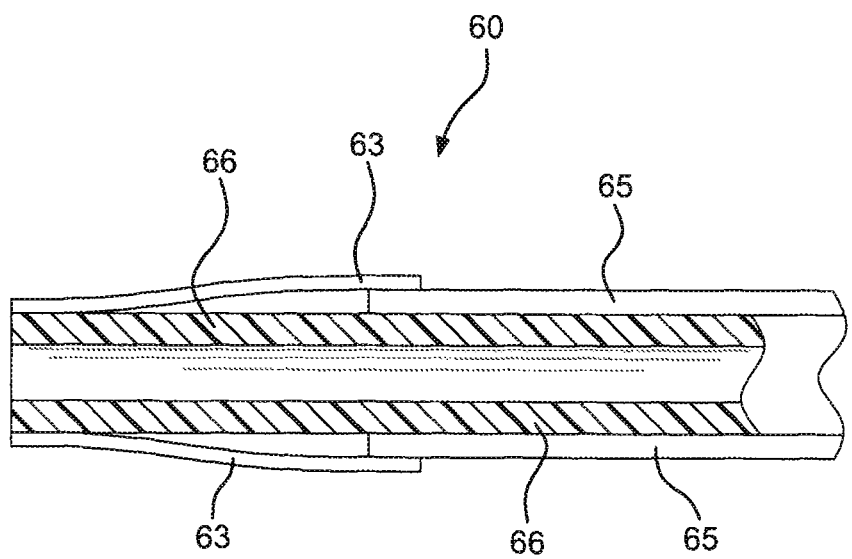
FIG. 25 illustrates an embodiment of the present invention.

Two flexible displacement elements (63) were attached to the inner tube (66) and outer tube (65) as illustrated in FIGS. 24 and 25. Each flexible displacement element (63) was made from a 7.5 cm length of a nickel-titanium alloy metal (Nitinol) wire (0.38 mm in diameter (Part Number SE508-NDC, Fremont, Calif.). One end of each Nitinol wire was attached to the inner tube approximately 5 mm from the exposed end. The other end of the Nitinol wire was attached to the outer tube approximately 5 mm from the end as shown in FIGS. 24 and 25. The wires were spaced approximately 120 degrees apart as illustrated in FIGS. 24 and 25.

The flexible displacement elements (63) were attached to the outer tube (65) and inner tube (66) by a potting method utilizing appropriately sized fluorinated ethylene propylene (FEP) shrink tubing (available from Zeus Mfg, Orangeburg, S.C.) and the application of localized heat. Once the flexible displacement elements (63) were attached to the inner tube (66) and outer tube (65), a catheter having flexible displacement elements was formed.

In practice, the inner tube (66) and outer tube (65) are positioned so the flexible displacement elements (63) are elongated and reside close to the catheter tubes (FIG. 25). When the outer tube (65) is moved over the inner tube (66), the flexible displacement elements (63) assumed a bowed configuration. In such a radially bowed configuration, the flexible displacement elements (63) can contact anatomical structures and aid in placement and use of a medical device associated with a catheter. For example, the bowed wires can contact an inside wall of a blood the vessel and stabilize the position of the assembly within the vessel lumen. The bowed flexible displacement elements can also exert force against the blood vessel wall to bias the catheter and any medical device or tool associated with the catheter in a direction that aids in the operation of the device or tool.

Example 6

This example describes the construction of an embodiment of the present invention (80) having a plurality of flexible displacement elements splayed around a common center element. At least one of the flexible displacement elements has a cutting blade or cutting hook attached thereto (FIGS. 26-29).

The flexible displacement elements (7) were made from a nickel-titanium alloy metal having "shape-memory" properties commonly referred to as nitinol. Nitinol wire (0.46 mm diameter) was obtained (SE508, Nitinol Devices and Components, Fremont, Calif.). The wire was cut into eight lengths, each approximately 10 cm long.

Each end of each flexible displacement element was attached to a collar component (81 and 82). In this embodiment, two collars (81 and 82) were constructed from an aluminum bar. The collars had the following dimensions: 2.67 mm inner diameter; 5 mm outer diameter; 3.18 mm thickness; and 8 evenly spaced 0.05 mm diameter holes around a 4.19 mm bolt circle (FIG. 20). The two collars (81, 82) were fit over the mid-section of a 2.54 mm diameter steel mandrel and spaced approximately 57.15 mm apart. Seven of the lengths of the nitinol wire were fit through opposing holes in the collars.

A small "gut hook" (83) was created with a channel at its base along its length. The geometry of the channel was such that it fit readily on one of the nitinol wires. The "hook" was designed with an internal, crescent shaped sharpened edge (FIG. 28). A portion of the "hook" is designed to act as a guide which presents a blunt, atraumatic surface to anatomical structures not intended to be severed or compromised. Once the guide portion is inserted through a fenestration, tension may be applied to the entire system, thus causing impingement of the sharpened portion against the anatomical structure to be cut (septum of the dissection). Tension provides the necessary cutting pressure while the leading "guide" portion of the "hook" remains in contact with the septum.

The eighth nitinol wire was positioned through the channel of the gut hook until the hook was located at mid-length of the nitinol wire. The nitinol wire was fit through the two (2) remaining opposing holes of the collars (81, 82).

Figure 29:
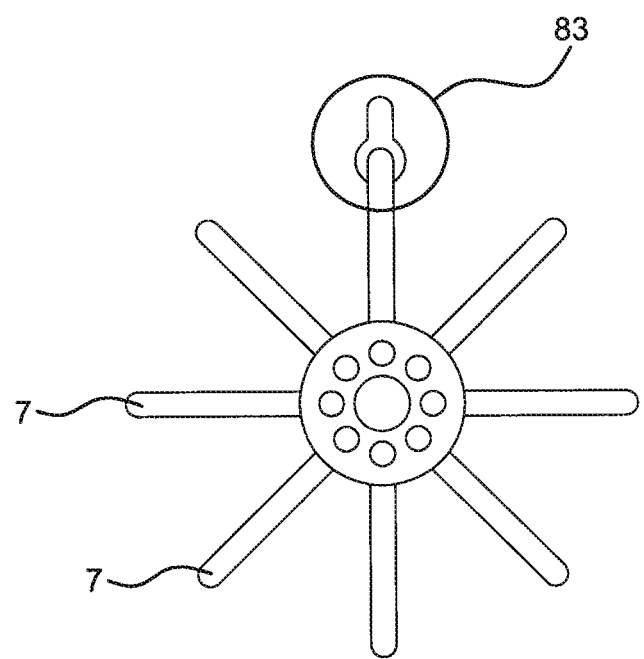
FIG. 29 illustrates an embodiment of the present invention.

The ends of the eight (8) lengths of wire were bundled together and secured to the mandrel with silver plated copper wire to form a nitinol wire basket assembly. The collars were forced together (along the mandrel) to create a fusiform bulge in the nitinol wire basket (FIG. 27). The diameter of the fusiform bulge was approximately 38 mm. The assembly was placed in a forced air oven set to 450 deg C. for 15 minutes following by quenching in water. The nitinol wires were then glued in place using cyanoacrylate glue and the ends of the nitinol wires were trimmed flush with the collars. The silver plated wire was removed and discarded. The gut hook was fixed in place at mid-length of the wire with cyanoacrylate glue and allowed to dry (FIGS. 28 and 29).

A biliary catheter was obtained (#VN 0804040, WL Gore & Associates, Flagstaff, Ariz.). A portion of the distal end of the outer catheter was removed to expose the inner catheter. A single-lumen polymer tube was obtained (Putnam Platsics, Dayville, Conn.). The polymer tube was approximately 57 cm in length, 4.78 mm in outer diameter and 3.90 mm inner diameter.

A handle was fabricated from a 4 mm disposable biopsy punch (available from Miltex Instrument Company, Lake Success, N.Y.). The cutting element of the punch was removed and the handle was reamed through its center to enable the single-lumen polymer tube to be inserted inside it. The fabricated "handle" was attached to one end of the single-lumen polymer tube with cyanoacrylate glue.

A section of FEP tubing was obtained (Zeus, Orangeburg, S.C.). The FEP tubing was approximately 10 cm long, 6.6 mm outer diameter, and 5.5 mm inner diameter. The FEP tubing was placed over the outer surface of the end of single-lumen polymer tube that was not attached to the handle and was secured with cyanoacrylate glue, thereby creating a constraining sheath (84). This constraining sheath (84) was designed to house the wire basket and gut hook during device delivery (FIG. 26). Retraction of the constraining sheath released the wire basket and the hook. The constraining sheath was positioned handle end first over the outer surface of the biliary catheter, but not attached.

With the constraining sheath butted against the hub at the proximal end of the biliary catheter, an approximately 100 mm length of the biliary outer catheter (6) tube remained uncovered by this sheath. One collar of the wire basket assembly was fitted over the outer sheath of the biliary catheter, fixed in placed with cyanoacrylate glue, and allowed to dry. The other collar was fitted over the inner member of the biliary catheter (2) spaced approximately 57 mm apart from the other collar, fixed in placed with cyanoacrylate glue, and allowed to dry.

The catheter outer sheath was advanced distally to constrain the basket inside the sheath at a profile suitable for endoluminal delivery. Retraction of the outer sheath released the basket, enabling it to spring open. Pulling the proximal end of the inner member causing it to move relative to the outer sheath served to further adjust the diameter of the basket.

Example 7

This example describes construction of an embodiment of the present invention (70) utilizing a partially insulated electrically energized wire (71), or filament, as a tissue cutting element. This embodiment also has a plurality of displacement elements (73) associated with the cutting end of the invention. The displacement elements (73) assist in positioning of the invention at a desired anatomical location. The displacement elements (73) also maintain the tissue cutting element in contact with tissue as tissue is being cut (FIG. 31).

A ninety-six centimeter (96 cm) length of PEBAX® tubing was obtained and used as a delivery catheter (72) for a partially insulated electrically conductive tissue cutting wire (71). The partially insulated electrically conductive tissue cutting wire (71) was made of Nitinol and was greater in length than the delivery catheter (72). The tip end of the partially insulated electrically conductive tissue cutting wire was bent into a hooked-shape (FIG. 30). At least one layer of electrically insulating material (71) was placed on the outer surface of substantially all the electrically conductive tissue cutting wire. As illustrated in FIGS. 30 and 31, a portion (74) of the electrically conductive tissue cutting wire was left uncovered with electrically insulating material. This un-insulated portion (74) of the electrically conductive tissue cutting wire was used to cut tissue when energized with an electric current provided by an RF electrocautery device As illustrated in FIG. 30, the partially insulated electrically conductive tissue cutting wire (71) is initially confined within the delivery catheter (72). In use, the partially insulated electrically conductive tissue cutting wire (71) is pushed out of the end of the delivery catheter and/or the delivery catheter is retracted from around the partially insulated electrically conductive tissue cutting wire (FIG. 23).

As illustrated in FIG. 30, at least two displacement elements (73) were also attached to the delivery catheter (72) and partially insulated electrically conductive tissue cutting wire (71). Each flexible displacement element (73) was made from a 7.5 cm length of a nickel-titanium alloy metal (Nitinol) wire (0.38 mm in diameter (Part Number SE508-NDC, Fremont, Calif.). One end of each Nitinol wire was attached to the delivery catheter (72) approximately 5 mm from the exposed end of the catheter. The other end of the Nitinol wire was attached to the partially insulated electrically conductive tissue cutting wire approximately 5 mm from the end as shown in FIG. 30. The wires were spaced approximately 120 degrees apart as illustrated in FIG. 14.

The flexible displacement elements (73) were attached to the delivery catheter (72) and partially insulated electrically conductive tissue cutting wire (71) by a potting method utilizing appropriately sized fluorinated ethylene propylene (FEP) shrink tubing (available from Zeus Mfg, Orangeburg, S.C.) and the application of localized heat. Once the flexible displacement elements (73) were attached to the delivery catheter (72) and partially insulated electrically conductive tissue cutting wire (71), a cutting catheter having flexible displacement elements was formed.

What is claimed is:

1. A method of treating an aortic dissection comprising:
   providing a medical cutting tool for cutting a tissue wall of a false lumen of a vessel, said medical cutting tool comprising:
      a catheter having an outer catheter tube, said outer catheter tube having a longitudinally extending lumen, said catheter having an inner member extending through said lumen;
      at least one displacement element having a first end attached to said inner member of said catheter and an opposite second end attached to said outer catheter tube, such that a middle portion of said at least one displacement element between said first and second ends can be displaced radially in response to relative axial movement between said inner member and said outer catheter tube;
      a cutting edge attached to said middle portion of said at least one displacement element and which displaces radially with said middle portion in response to relative axial movement between said inner member and outer catheter tube;
      a collar attached to each of said first and second ends of said at least one displacement element, wherein said collar on said first end of said at least one displacement element is attached to said inner member of said catheter and said collar on said second end of said at least one displacement element is attached to said outer catheter tube; and
      a hook fixedly secured to said middle portion of said at least one displacement element, said hook having an atraumatic surface, said cutting edge formed along a portion of said hook opposite said atraumatic surface;
   placing said catheter within an arterial system;
   advancing said catheter through said arterial system to a location distal to a primary entry tear of said aortic dissection;
   contacting aortic tissue with said at least one displacement element;
   engaging said cutting edge of said hook with a septum; and
   advancing said cutting edge along said septum.

2. The method of claim 1 including cannulating a guidewire from said catheter through a hole in a tissue of said aortic dissection into a false lumen delimited by septal tissue prior to advancing said catheter.

3. The method of claim 1 including radially displacing said hook relative to said catheter by axially moving said inner member and said outer catheter tube relative to each other.

4. The method of claim 1 further comprising removing said catheter from said arterial system.

* * * * *